(12) United States Patent
Schmidt et al.

(10) Patent No.: US 11,691,006 B2
(45) Date of Patent: Jul. 4, 2023

(54) ELECTRICAL STIMULATION DEVICES FOR CANCER TREATMENT

(71) Applicant: Boston Scientific Scimed, Inc., Maple Grove, MN (US)

(72) Inventors: Brian L. Schmidt, White Bear Lake, MN (US); Devon N. Arnholt, Shoreview, MN (US); Benjamin Keith Stein, Shoreview, MN (US); Keith R. Maile, New Brighton, MN (US); William J. Linder, Golden Valley, MN (US); Ron A. Balczewski, Bloomington, MN (US); Aleksandra Kharam, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 16/850,712

(22) Filed: Apr. 16, 2020

(65) Prior Publication Data

US 2020/0330756 A1    Oct. 22, 2020

Related U.S. Application Data

(60) Provisional application No. 62/837,125, filed on Apr. 22, 2019.

(51) Int. Cl.
*A61N 1/36* (2006.01)
*A61B 5/0538* (2021.01)
*A61N 1/05* (2006.01)

(52) U.S. Cl.
CPC ........ *A61N 1/36002* (2017.08); *A61B 5/0538* (2013.01); *A61N 1/05* (2013.01)

(58) Field of Classification Search
CPC ........ A61N 1/36002; A61N 1/05; A61N 1/06; A61N 1/32; A61B 5/0538
See application file for complete search history.

(56) References Cited

U.S. PATENT DOCUMENTS

| | | | |
|---|---|---|---|
| 4,016,886 | A | 4/1977 | Doss et al. |
| 5,099,838 | A | 3/1992 | Bardy |

(Continued)

FOREIGN PATENT DOCUMENTS

| | | |
|---|---|---|
| AU | 2005301103 | 5/2006 |
| CN | 101693875 | 4/2010 |

(Continued)

OTHER PUBLICATIONS

"Decision of Rejection," for Japanese Patent Application No. 2020-54219 dated Oct. 19, 2021 (6 pages) with English Translation.

(Continued)

*Primary Examiner* — Mark W. Bockelman
(74) *Attorney, Agent, or Firm* — Pauly, DeVries Smith & Deffner LLC

(57) ABSTRACT

Embodiments herein relate to a medical device for treating a cancerous tumor, the medical device having a first lead including a first wire and second wire; a second lead can include a third wire and fourth wire; and a first electrode in electrical communication with the first wire, a second electrode in electrical communication with the second wire, a third electrode in electrical communication with the third wire, and a fourth electrode in electrical communication with the fourth wire. The first and third electrodes form a supply electrode pair configured to deliver one or more electric fields to the cancerous tumor. The second and fourth electrodes form a sensing electrode pair configured to measure an impedance of the cancerous tumor independent of an impedance of the first electrode, the first wire, the third electrode, the third wire, and components in electrical communication therewith. Other embodiments are also included herein.

8 Claims, 14 Drawing Sheets

(56) References Cited

U.S. PATENT DOCUMENTS

| | | |
|---|---|---|
| 5,324,328 A | 6/1994 | Li et al. |
| 5,397,342 A | 3/1995 | Heil et al. |
| 5,458,597 A | 10/1995 | Edwards et al. |
| 5,582,609 A | 12/1996 | Swanson et al. |
| 5,834,051 A | 11/1998 | Woloszko et al. |
| 6,366,808 B1 | 4/2002 | Schroeppel et al. |
| 6,673,623 B1 | 1/2004 | Huberman |
| 6,868,289 B2 | 3/2005 | Palti |
| 6,920,361 B2 | 7/2005 | Williams |
| 7,162,310 B2 | 1/2007 | Doan |
| 7,524,274 B2 | 4/2009 | Patrick et al. |
| 7,565,205 B2 | 7/2009 | Palti |
| 7,656,205 B2 | 2/2010 | Chen et al. |
| 7,715,921 B2 | 5/2010 | Palti |
| 7,720,549 B2 | 5/2010 | Schroeppel et al. |
| 7,805,201 B2 | 9/2010 | Palti |
| 7,809,441 B2 | 10/2010 | Kane et al. |
| 7,890,183 B2 | 2/2011 | Palti et al. |
| 7,917,227 B2 | 3/2011 | Palti |
| 8,002,821 B2 | 8/2011 | Stinson |
| 8,019,414 B2 | 9/2011 | Palti |
| 8,170,648 B2 | 5/2012 | Field et al. |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,483,821 B2 | 7/2013 | Averina et al. |
| 8,500,713 B2 | 8/2013 | Ferek-petric |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 8,805,466 B2 | 8/2014 | Salahieh et al. |
| 8,956,352 B2 | 2/2015 | Mauch et al. |
| 9,005,100 B2 | 4/2015 | Gnanashanmugam et al. |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,179,974 B2 | 11/2015 | Ku et al. |
| 9,248,278 B2 | 2/2016 | Crosby et al. |
| 9,283,383 B2 | 3/2016 | Osypka |
| 9,308,039 B2 | 4/2016 | Azure |
| 9,387,323 B2 | 7/2016 | Fleischhacker et al. |
| 9,427,278 B2 | 8/2016 | Swanson |
| 9,440,068 B2 | 9/2016 | Palti et al. |
| 9,526,911 B1 | 12/2016 | Azure et al. |
| 9,630,022 B2 | 4/2017 | Bourke et al. |
| 9,655,669 B2 | 5/2017 | Palti et al. |
| 9,750,934 B2 | 9/2017 | Palti et al. |
| 9,833,617 B2 | 12/2017 | Travers et al. |
| 9,910,453 B2 | 3/2018 | Wasserman et al. |
| 10,029,117 B2 | 7/2018 | Bourke |
| 10,238,862 B2 * | 3/2019 | Cook ............... A61N 1/36146 |
| 10,265,530 B1 * | 4/2019 | Perryman ............... A61N 1/05 |
| 10,376,177 B2 | 8/2019 | Valvano et al. |
| 10,471,254 B2 | 11/2019 | Sano et al. |
| 11,191,956 B2 | 12/2021 | Giladi et al. |
| 11,331,493 B2 | 5/2022 | Pivonka et al. |
| 11,338,135 B2 | 5/2022 | Schmidt et al. |
| 11,420,049 B2 | 8/2022 | Schmidt et al. |
| 11,607,542 B2 | 3/2023 | Schmidt et al. |
| 2001/0044643 A1 | 11/2001 | Litovitz |
| 2002/0026183 A1 | 2/2002 | Simpson |
| 2002/0049485 A1 | 4/2002 | Smits |
| 2002/0065544 A1 | 5/2002 | Smits |
| 2003/0020416 A1 | 1/2003 | Kobayashi |
| 2003/0069623 A1 | 4/2003 | Stypulkowski |
| 2003/0204161 A1 | 10/2003 | Ferek-Petric |
| 2004/0010290 A1 | 1/2004 | Schroeppel et al. |
| 2004/0158288 A1 | 8/2004 | Keisari et al. |
| 2004/0176804 A1 | 9/2004 | Palti |
| 2004/0215296 A1 | 10/2004 | Ganz et al. |
| 2005/0004507 A1 | 1/2005 | Schroeppel et al. |
| 2005/0043894 A1 | 2/2005 | Fernandez |
| 2005/0096584 A1 | 5/2005 | Ferek-petric |
| 2005/0209642 A1 | 9/2005 | Palti |
| 2005/0222623 A1 | 10/2005 | Kroll et al. |
| 2005/0222646 A1 | 10/2005 | Kroll et al. |
| 2005/0240173 A1 | 10/2005 | Palti |
| 2005/0288730 A1 | 12/2005 | Deem et al. |
| 2006/0024802 A1 | 2/2006 | Muller et al. |
| 2006/0149341 A1 | 7/2006 | Palti |
| 2006/0190053 A1 | 8/2006 | Dobak |
| 2006/0282122 A1 | 12/2006 | Palti |
| 2007/0033660 A1 | 2/2007 | Palti |
| 2007/0179550 A1 | 8/2007 | Dennis et al. |
| 2007/0225766 A1 | 9/2007 | Palti |
| 2007/0239213 A1 | 10/2007 | Palti |
| 2007/0239244 A1 | 10/2007 | Morgan et al. |
| 2007/0270675 A1 | 11/2007 | Kane et al. |
| 2007/0270916 A1 | 11/2007 | Fischell et al. |
| 2008/0058669 A1 | 3/2008 | Kroll |
| 2008/0071350 A1 | 3/2008 | Stinson et al. |
| 2008/0086073 A1 | 4/2008 | McDaniel |
| 2008/0097424 A1 | 4/2008 | Wizeman et al. |
| 2008/0195227 A1 | 8/2008 | Boling et al. |
| 2008/0208271 A1 | 8/2008 | Sih et al. |
| 2008/0275524 A1 | 11/2008 | Furness et al. |
| 2009/0076500 A1 | 3/2009 | Azure et al. |
| 2009/0192381 A1 | 7/2009 | Brockway et al. |
| 2009/0234211 A1 | 9/2009 | Li et al. |
| 2010/0016936 A1 | 1/2010 | Stevenson et al. |
| 2010/0198298 A1 | 8/2010 | Schulman et al. |
| 2010/0261994 A1 | 10/2010 | Davalos et al. |
| 2010/0298895 A1 | 11/2010 | Ghaffari et al. |
| 2010/0331938 A1 | 12/2010 | Sommer et al. |
| 2011/0125215 A1 | 5/2011 | Goetz et al. |
| 2011/0137229 A1 | 6/2011 | Palti et al. |
| 2011/0238057 A1 | 9/2011 | Moss et al. |
| 2012/0035616 A1 | 2/2012 | Olsen et al. |
| 2012/0130444 A1 | 5/2012 | Wei et al. |
| 2012/0158072 A1 | 6/2012 | Venook et al. |
| 2012/0158122 A1 | 6/2012 | Mattson et al. |
| 2012/0203307 A1 | 8/2012 | Schroeppel et al. |
| 2012/0232615 A1 | 9/2012 | Barolat et al. |
| 2012/0283726 A1 | 11/2012 | Palti |
| 2013/0023946 A1 | 1/2013 | Valvano et al. |
| 2013/0165916 A1 | 6/2013 | Mathur et al. |
| 2013/0204068 A1 | 8/2013 | Gnanashanmugam et al. |
| 2013/0261706 A1 | 10/2013 | Mirro et al. |
| 2013/0261711 A1 | 10/2013 | Sivo |
| 2013/0289649 A1 | 10/2013 | Averina et al. |
| 2013/0289664 A1 | 10/2013 | Johanek |
| 2013/0310898 A1 | 11/2013 | Ollivier et al. |
| 2014/0005753 A1 | 1/2014 | Carbunaru |
| 2014/0052227 A1 | 2/2014 | Wahlstrand et al. |
| 2014/0107511 A1 | 4/2014 | Banet et al. |
| 2014/0142670 A1 | 5/2014 | Radhakrishnan et al. |
| 2014/0276781 A1 | 9/2014 | Beani et al. |
| 2014/0276811 A1 | 9/2014 | Koblish et al. |
| 2014/0350653 A1 | 11/2014 | Shiroff et al. |
| 2015/0005804 A1 | 1/2015 | Franano et al. |
| 2015/0066024 A1 | 3/2015 | Azure |
| 2015/0134022 A1 | 5/2015 | Lee et al. |
| 2015/0180161 A1 | 6/2015 | Olson et al. |
| 2015/0320995 A1 | 11/2015 | Nazareth et al. |
| 2015/0374992 A1 | 12/2015 | Crosby et al. |
| 2016/0022986 A1 | 1/2016 | Travers et al. |
| 2016/0029960 A1 | 2/2016 | Toth et al. |
| 2016/0068598 A1 | 3/2016 | Yan et al. |
| 2016/0082258 A1 | 3/2016 | Kramer et al. |
| 2016/0128767 A1 | 5/2016 | Azamian et al. |
| 2016/0129276 A1 | 5/2016 | Fried et al. |
| 2016/0250476 A1 * | 9/2016 | Kaemmerer ....... A61N 1/37247 607/45 |
| 2016/0250483 A1 | 9/2016 | Klimovitch et al. |
| 2016/0331459 A1 | 11/2016 | Townley et al. |
| 2016/0346536 A1 | 12/2016 | Palti et al. |
| 2017/0007310 A1 | 1/2017 | Rajagopalan et al. |

(56) References Cited

U.S. PATENT DOCUMENTS

| | | |
|---|---|---|
| 2017/0035496 A1 | 2/2017 | Nagale et al. |
| 2017/0049514 A1 | 2/2017 | Cosman |
| 2017/0065339 A1 | 3/2017 | Mickelsen |
| 2017/0105793 A1 | 4/2017 | Cao et al. |
| 2017/0120041 A1 | 5/2017 | Wenger et al. |
| 2017/0173340 A1 | 6/2017 | Gupte et al. |
| 2017/0189098 A1 | 7/2017 | Azure et al. |
| 2017/0215939 A1 | 8/2017 | Palti et al. |
| 2017/0251976 A1 | 9/2017 | Schouenborg |
| 2017/0266371 A1 | 9/2017 | Leonhardt et al. |
| 2017/0281934 A1 | 10/2017 | Giladi et al. |
| 2017/0281955 A1 | 10/2017 | Maile et al. |
| 2017/0312501 A1 | 11/2017 | Bornzin et al. |
| 2017/0333702 A1 | 11/2017 | Barner |
| 2018/0001075 A1 | 1/2018 | Kirson et al. |
| 2018/0001078 A1 | 1/2018 | Kirson et al. |
| 2018/0008708 A1 | 1/2018 | Giladi et al. |
| 2018/0021563 A1 | 1/2018 | Van De Stolpe et al. |
| 2018/0050200 A1 | 2/2018 | Wasserman et al. |
| 2018/0110978 A1 | 4/2018 | Beebe et al. |
| 2018/0154142 A1 | 6/2018 | Guo et al. |
| 2018/0221088 A1 | 8/2018 | Govari et al. |
| 2018/0246079 A1 | 8/2018 | Wang et al. |
| 2018/0289954 A1 | 10/2018 | Hebb et al. |
| 2019/0008555 A1 | 1/2019 | O'mahony |
| 2019/0117969 A1 | 4/2019 | Schmidt et al. |
| 2019/0117970 A1 | 4/2019 | Schmidt et al. |
| 2019/0117971 A1 | 4/2019 | Schmidt et al. |
| 2019/0117972 A1 | 4/2019 | Schmidt et al. |
| 2019/0117973 A1 | 4/2019 | Schmidt et al. |
| 2019/0255344 A1 | 8/2019 | Carter et al. |
| 2020/0009377 A1 | 1/2020 | Chang et al. |
| 2020/0330757 A1 | 10/2020 | Schmidt et al. |
| 2020/0330758 A1 | 10/2020 | Schmidt et al. |
| 2020/0338344 A1 | 10/2020 | Schmidt et al. |
| 2020/0338345 A1 | 10/2020 | Schmidt et al. |
| 2020/0338346 A1 | 10/2020 | Schmidt et al. |
| 2021/0260370 A1 | 8/2021 | Srivastava et al. |
| 2022/0241586 A1 | 8/2022 | Spehr et al. |
| 2022/0296907 A1 | 9/2022 | Schmidt et al. |

FOREIGN PATENT DOCUMENTS

| | | |
|---|---|---|
| CN | 202365923 | 8/2012 |
| CN | 204698678 | 10/2015 |
| CN | 106823145 | 6/2017 |
| CN | 111263618 | 6/2020 |
| CN | 111263656 | 6/2020 |
| CN | 111278504 | 6/2020 |
| CN | 111432872 | 7/2020 |
| CN | 111465429 | 7/2020 |
| EP | 2942023 | 11/2015 |
| EP | 3700451 | 9/2020 |
| EP | 3700621 | 9/2020 |
| EP | 3700623 | 9/2020 |
| EP | 3700626 | 9/2020 |
| EP | 3700627 | 9/2020 |
| TW | 201039699 | 11/2010 |
| WO | 9513113 | 5/1995 |
| WO | 9526911 | 10/1995 |
| WO | 9639966 | 12/1996 |
| WO | 0158371 | 8/2001 |
| WO | 0167098 | 9/2001 |
| WO | 2005115535 | 12/2005 |
| WO | 2006047833 | 5/2006 |
| WO | 2008089360 | 7/2008 |
| WO | 2009036457 | 3/2009 |
| WO | 2009036459 | 3/2009 |
| WO | 2013052590 | 4/2013 |
| WO | 2015100451 | 7/2015 |
| WO | 2016065263 | 4/2016 |
| WO | 2016149575 | 9/2016 |
| WO | 2016168485 | 10/2016 |
| WO | 2016179712 | 11/2016 |
| WO | 2016199142 | 12/2016 |
| WO | 2017123981 | 7/2017 |
| WO | 2018207103 | 11/2018 |
| WO | 2019084003 | 5/2019 |
| WO | 2019084011 | 5/2019 |
| WO | 2019084013 | 5/2019 |
| WO | 2019084016 | 5/2019 |
| WO | 2019084021 | 5/2019 |
| WO | 2020219336 | 10/2020 |
| WO | 2020219337 | 10/2020 |
| WO | 2020219339 | 10/2020 |
| WO | 2020219517 | 10/2020 |
| WO | 2020219519 | 10/2020 |
| WO | 2020219521 | 10/2020 |

OTHER PUBLICATIONS

"Final Office Action," for U.S. Appl. No. 16/167,140 dated Dec. 27, 2021 (30 pages).

"Non-Final Office Action," for U.S. Appl. No. 16/166,957 dated Dec. 22, 2021 (39 pages).

"Non-Final Office Action," for U.S. Appl. No. 16/167,087 dated Dec. 22, 2021 (24 pages).

"Office Action," for Japanese Patent Application No. 2020-542721 dated Jan. 4, 2022 (2 pages) No English Translation.

"Response to Communication Pursuant to Art. 94(3) EPC," for European Patent Application No. 18801137.3 filed Jan. 13, 2022 (8 pages).

"Response to Final Rejection," dated Nov. 5, 2021 for U.S. Appl. No. 16/855,421, submitted via EFS-Web on Jan. 5, 2022, 11 pages.

"Response to Office Action," for Canadian Patent Application No. 3,079,316 filed Dec. 31, 2021 (15 pages).

"Communication Pursuant to Article 94(3) EPC," for European Patent Application No. 18801137.3 dated Sep. 15, 2021 (4 pages).

"Decision of Rejection," for Japanese Patent Application No. 2020-542719 dated Oct. 19, 2021 (3 pages) No English Translation.

"Final Office Action," for U.S. Appl. No. 16/850,720 dated Nov. 15, 2021 (15 pages).

"Final Office Action," for U.S. Appl. No. 16/855,421 dated Nov. 5, 2021 (25 pages).

"First Office Action," for Chinese Patent Application No. 201880078117.8 dated Jul. 20, 2021 (14 pages) with English Summary.

"International Preliminary Report on Patentability," for PCT Application No. PCT/US2020/028508 dated Nov. 4, 2021 (8 pages).

"International Preliminary Report on Patentability," for PCT Application No. PCT/US2020/028509 dated Nov. 4, 2021 (9 pages).

"International Preliminary Report on Patentability," for PCT Application No. PCT/US2020/028512 dated Nov. 4, 2021 (8 pages).

"International Preliminary Report on Patentability," for PCT Application No. PCT/US2020/029270 dated Nov. 4, 2021 (11 pages).

"International Preliminary Report on Patentability," for PCT Application No. PCT/US2020/029274 dated Nov. 4, 2021 (13 pages).

"International Preliminary Report on Patentability," for PCT Application No. PCT/US2020/029277 dated Nov. 4, 2021 (10 pages).

"Non-Final Office Action," for U.S. Appl. No. 16/167,116 dated Sep. 3, 2021 (29 pages).

"Non-Final Office Action," for U.S. Appl. No. 16/850,720 dated Aug. 24, 2021 (32 pages).

"Non-Final Office Action," for U.S. Appl. No. 16/855,433 dated Sep. 8, 2021 (32 pages).

"Office Action," for Canadian Patent Application No. 3,079,316 dated Oct. 27, 2021 (4 pages).

"Office Action," for Japanese Patent Application No. 2020-542718 dated Oct. 19, 2021 (3 pages) No English Translation.

"Office Action," for Japanese Patent Application No. 2020-542722 dated Oct. 26, 2021 (5 pages) No English Translation.

"Response to Communication Pursuant to Article 94(3) EPC," for European Patent Application No. 18801138.1 filed Oct. 15, 2021 (10 pages).

"Response to Examination Report," for Canadian Patent Application No. 3,079,213 filed Nov. 10, 2021 (13 pages).

"Response to Examination Report," for Canadian Patent Application No. 3,079,282 filed Nov. 10, 2021 (13 pages).

(56) References Cited

OTHER PUBLICATIONS

"Response to Final Rejection mailed on," dated Aug. 2, 2021 for U.S. Appl. No. 16/167,087, submitted via EFS-Web on Nov. 1, 2021, 12 pages.
"Response to Final Rejection," dated Jun. 23, 2021 and the Advisory Action dated Oct. 15, 2021 for U.S. Appl. No. 16/167,079, submitted via EFS-Web on Oct. 21, 2021, 19 pages.
"Response to Final Rejection," dated Jun. 23, 2021 for U.S. Appl. No. 16/167,079, submitted via EFS-Web on Sep. 9, 2021, 16 pages.
"Response to Final Rejection," dated May 14, 2021 and Advisory Action dated Aug. 26, 2021 for U.S. Appl. No. 16/166,957, submitted via EFS-Web on Sep. 10, 2021.
"Response to Non-Final Rejection," dated Aug. 24, 2021 for U.S. Appl. No. 16/850,720, submitted via EFS-Web on Nov. 1, 2021, 11 pages.
"Response to Non-Final Rejection," dated Jul. 12, 2021 for U.S. Appl. No. 16/167,140, submitted via EFS-Web on Oct. 12, 2021, 16 pages.
"Response to Non-Final Rejection," dated May 28, 2021 for U.S. Appl. No. 16/855,421, submitted via EFS-Web on Aug. 20, 2021, 11 pages.
"Response to Non-Final Rejection," dated Sep. 3, 2021 for U.S. Appl. No. 16/167,116, submitted via EFS-Web on Nov. 2, 2021, 14 pages.
"Response to Non-Final Rejection," dated Sep. 8, 2021 for U.S. Appl. No. 16/855,433, submitted via EFS-Web on Nov. 2, 2021, 12 pages.
"Response to Office Action," for Canadian Patent Application No. 3,079,314 filed Nov. 12, 2021 (14 pages).
"Response to Office Action," for Canadian Patent Application No. 3,079,289 filed with CIPO Sep. 23, 2021 (17 pages).
"Second Office Action," for Chinese Patent Application No. 201880068896.3 dated Oct. 20, 2021 (6 pages), no English translation.
"Optune®—Elevate Expectations / Patient Information and Operation Manual," Novocure™, www.optune.com, 46, pages, Jan. 2019.
Di Sebastiano, Andrea R. et al., "Preclinical Outcomes of Intratumoral Modulation Therapy for Glioblastoma," Scientific Reports (2018) 8:7301 (11 pages).
File History for U.S. Appl. No. 16/166,957 downloaded Dec. 28, 2020 (427 pages).
File History for U.S. Appl. No. 16/167,079 downloaded Dec. 28, 2020 (301 pages).
File History for U.S. Appl. No. 16/167,087 downloaded Dec. 28, 2020 (310 pages).
File History for U.S. Appl. No. 16/167,116 downloaded Dec. 28, 2020 (238 pages).
File History for U.S. Appl. No. 16/167,140 downloaded Dec. 28, 2020 (231 pages).
"First Examination Report," for Australian Patent Application No. 2018354149 dated Jul. 29, 2020 (5 pages).
"First Examination Report," for Australian Patent Application No. 2018354157 dated Jul. 31, 2020 (5 pages).
"First Examination Report," for Australian Patent Application No. 2018354159 dated Aug. 12, 2020 (5 pages).
"First Examination Report," for Australian Patent Application No. 2018354162 dated Sep. 29, 2020 (8 pages).
"First Examination Report," for Australian Patent Application No. 2018354167 dated Sep. 14, 2020 (5 pages).
"International Preliminary Report on Patentability," for PCT Application No. PCT/US2018/057104 dated May 7, 2020 (8 pages).
"International Preliminary Report on Patentability," for PCT Application No. PCT/US2018/057115 dated May 7, 2020 (9 pages).
"International Preliminary Report on Patentability," for PCT Application No. PCT/US2018/057117 dated May 7, 2020 (8 pages).
"International Preliminary Report on Patentability," for PCT Application No. PCT/US2018/057120 dated May 7, 2020 (8 pages).
"International Preliminary Report on Patentability," for PCT Application No. PCT/US2018/057127 dated May 7, 2020 (8 pages).
"International Search Report and Written Opinion," for PCT Application No. PCT/US2018/057104 dated Dec. 20, 2018 (14 pages).
"International Search Report and Written Opinion," for PCT Application No. PCT/US2018/057115 dated Jan. 4, 2019 (13 pages).
"International Search Report and Written Opinion," for PCT Application No. PCT/US2018/057117 dated Dec. 20, 2018 (14 pages).
"International Search Report and Written Opinion," for PCT Application No. PCT/US2018/057120 dated Dec. 19, 2018 (14 pages).
"International Search Report and Written Opinion," for PCT Application No. PCT/US2018/057127 dated Jan. 18, 2019 (12 pages).
"International Search Report and Written Opinion," for PCT Application No. PCT/US2020/028508 dated Aug. 3, 2020 (13 pages).
"International Search Report and Written Opinion," for PCT Application No. PCT/US2020/028509 dated Jun. 30, 2020 (15 pages).
"International Search Report and Written Opinion," for PCT Application No. PCT/US2020/028512 dated Jul. 13, 2020 (14 pages).
"International Search Report and Written Opinion," for PCT Application No. PCT/US2020/029270 dated Oct. 26, 2020 (19 pages).
"International Search Report and Written Opinion," for PCT Application No. PCT/US2020/029274 dated Aug. 28, 2020 (19 pages).
"International Search Report and Written Opinion," for PCT Application No. PCT/US2020/029277 dated Jul. 13, 2020 (15 pages).
"Invitation to Pay Additional Fees," for PCT Application No. PCT/US2020/029270 dated Aug. 28, 2020 (14 pages).
"Invitation to Pay Additional Fees," for PCT Application No. PCT/US2020/029274 dated Jul. 7, 2020 (13 pages).
Kirson, Eilon D. et al., "Disruption of Cancer Cell Replication by Alternating Electric Fields," Cancer Research 64, 3288-3295, May 1, 2004 (8 pages).
"Novocure Announces Launch of the inovitro™," Laboratory Research System, Press Release, 2 pages, Nov. 21, 2013., 2 pages.
"Response to Communication Pursuant to Rules 161(1) and 162 EPC," for European Patent Application No. 18800411.3 filed Dec. 9, 2020 (11 pages).
"Response to Communication Pursuant to Rules 161(1) and 162 EPC," for European Patent Application No. 18801134.0 filed Dec. 11, 2020 (9 pages).
"Response to Communication Pursuant to Rules 161(1) and 162 EPC," for European Patent Application No. 18801136.5 filed Dec. 10, 2020 (8 pages).
"Response to Communication Pursuant to Rules 161(1) and 162 EPC," for European Patent Application No. 18801137.3 filed Dec. 10, 2020 (7 pages).
"Response to Communication Pursuant to Rules 161(1) and 162 EPC," for European Patent Application No. 18801138.1 filed Dec. 11, 2020 (16 pages).
"Response to Examination Report," for Australian Patent Application No. 201354157 filed Dec. 31, 2020 (17 pages).
"Response to Examination Report," for Australian Patent Application No. 2018354149 filed Dec. 21, 2020 (14 pages).
Wang, Lijun et al., "Tumour Cell Membrane Poration and Ablation by Pulsed Low-Intensity Electric Field with Carbon Nanotubes," Int. J. Mol. Sci. 2015, 16, 6890-6901 (12 pages).
Xu, Hu et al., "In Vitro Validation of Intratumoral Modulation Therapy for Glioblastoma," Anticancer Research 36:71-80 (2016), 10 pages.
"Communication Pursuant to Article 94(3) EPC," for European Patent Application No. 18801138.1 dated Jun. 7, 2021 (7 pages).
"Examination Report," for Australian Patent Application No. 2018354162 dated Apr. 21, 2021 (5 pages).
"Examination Report," for Canadian Patent Application No. 3,079,213 dated Jul. 12, 2021 (4 pages).
"Examination Report," for Canadian Patent Application No. 3,079,282 dated Jul. 14, 2021 (4 pages).
"Examination Report," for Canadian Patent Application No. 3,079,314 dated Jul. 14, 2021 (4 pages).
"Final Office Action," for U.S. Appl. No. 16/166,957 dated May 14, 2021 (33 pages).
"Final Office Action," for U.S. Appl. No. 16/167,079 dated Jun. 23, 2021 (34 pages).
"Final Office Action," for U.S. Appl. No. 16/167,087 dated Aug. 2, 2021 (25 pages).

(56) References Cited

OTHER PUBLICATIONS

"First Office Action," for Chinese Patent Application No. 201880068896.3 dated Apr. 13, 2021 (17 pages) with English Summary.
"International Search Report and Written Opinion," for PCT Application No. PCT/US2021/019160 dated Jun. 2, 2021 (15 pages).
"Non-Final Office Action," for U.S. Appl. No. 16/167,140 dated Jul. 12, 2021 (32 pages).
"Non-Final Office Action," for U.S. Appl. No. 16/855,421 dated May 28, 2021 (37 pages).
"Office Action," for Canadian Patent Application No. 3,079,289 dated May 28, 2021 (4 pages).
"Office Action," for Japanese Patent Application No. 2020-542719 dated Jun. 1, 2021 (9 pages) with English Translation.
"Office Action," for Japanese Patent Application No. 2020-542720 dated May 11, 2021 (13 pages) with English Translation.
"Response to Examination Report," for Australian Patent Application No. 2018354162 filed Jul. 13, 2021 (18 pages).
"Response to Final Rejection," dated May 14, 2021 for U.S. Appl. No. 16/166,957, submitted via EFS-Web on Aug. 5, 2021, 18 pages.
"Response to Non-Final Rejection," dated Mar. 31, 2021 for U.S. Appl. No. 16/167,087, submitted via EFS-Web on Jun. 23, 2021, 12 pages.
"Communication Pursuant to Article 94(3) EPC," for European Patent Application No. 18801137.3 dated Mar. 5, 2021 (4 pages).
"Examination Report," for Australian Patent Application No. 2018354162 dated Feb. 4, 2021 (5 pages).
"Final Office Action," for U.S. Appl. No. 16/167,116 dated Jan. 21, 2021 (25 pages).
Giladi, Moshe et al., "Mitotic Spindle Disruption by Alternating Electric Fields Leads to Improper Chromosome Segregation and Mitotic Catastrophe in Cancer Cells," Sci Rep 5, 18046 (2016), 16 pages.
"Non-Final Office Action," for U.S. Appl. No. 16/166,957 dated Feb. 17, 2021 (37 pages).
"Non-Final Office Action," for U.S. Appl. No. 16/167,079 dated Jan. 6, 2021 (28 pages).
"Non-Final Office Action," for U.S. Appl. No. 16/167,087 dated Mar. 31, 2021 (28 pages).
"Office Action," for Japanese Patent Application No. 2020-542718 dated Feb. 9, 2021 11 pages) with English Translation.
"Office Action," for Japanese Patent Application No. 2020-542721 dated Feb. 9, 2021 (10 pages) with English Summary.
"Office Action," for Japanese Patent Application No. 2020-542722 dated Feb. 9, 2021 (5 pages) with English Summary.
"Response to Examination Report," for Australian Patent Application No. 2018354159 filed Jan. 18, 2021 (21 pages).
"Response to Examination Report," for Australian Patent Application No. 2018354162 filed Jan. 28, 2021 (15 pages).
"Response to Examination Report," for Australian Patent Application No. 2018354162 filed Mar. 30, 2021 (15 pages).
"Response to Examination Report," for Australian Patent Application No. 2018354167 filed Jan. 28, 2021 (17 pages).
"Response to Final Rejection," dated Jan. 21, 2021 for U.S. Appl. No. 16/167,116, submitted via EFS-Web on Mar. 2, 2021, 12 pages.
"Response to Final Rejection," dated Oct. 13, 2020 for U.S. Appl. No. 16/167,087, 11 pages, submitted via EFS-Web on Jan. 13, 2021.
"Response to Final Rejection," dated Oct. 19, 2020 for U.S. Appl. No. 16/167,140, submitted via EFS-Web on Jan. 19, 2021, 16 pages.
"Response to Non-Final Rejection," dated Feb. 17, 2021 for U.S. Appl. No. 16/166,957, submitted via EFS-Web on Mar. 17, 2021, 17 pages.
"Response to Non-Final Rejection," dated Jan. 6, 2021 for U.S. Appl. No. 16/267,079, submitted via EFS-Web on Apr. 6, 2021, 19 pages.
"Response to Non-Final Rejection," dated Oct. 7, 2020 for U.S. Appl. No. 16/167,116, submitted via EFS-Web on Jan. 6, 2021, 13 pages.
"Response to Second Examination Report," for Australian Patent Application No. 2018354149 filed Apr. 13, 2021 (19 pages).
"Second Examination Report," for Australian Patent Application No. 2018354149 dated Jan. 8, 2021 (4 pages).
"Final Office Action," for U.S. Appl. No. 16/166,957 dated May 18, 2022 (35 pages).
"Final Office Action," for U.S. Appl. No. 16/167,079 dated May 27, 2022 (29 pages).
"Final Office Action," for U.S. Appl. No. 16/167,087 dated May 18, 2022 (26 pages).
"Non-Final Office Action," for U.S. Appl. No. 16/167,140 dated May 27, 2022 (25 pages).
"Non-Final Office Action," for U.S. Appl. No. 16/855,421 dated Jun. 7, 2022 (21 pages).
"Non-Final Office Action," for U.S. Appl. No. 16/855,433 dated May 27, 2022 (18 pages).
"Notice of Allowance," for U.S. Appl. No. 16/850,720 dated Apr. 14, 2022 (17 pages).
"Office Action," for Canadian Patent Application No. 3,079,213 dated Apr. 20, 2022 (6 pages).
"Office Action," for Canadian Patent Application No. 3,079,289 dated Mar. 24, 2022 (8 pages).
"Office Action," for Canadian Patent Application No. 3,079,314 dated Apr. 29, 2022 (3 pages).
"Response to Communication Pursuant to Rules 161(1) and 162 EPC," for European Patent Application No. 20724332.0 filed May 11, 2022 (24 pages).
"Response to Communication Pursuant to Rules 161(1) and 162 EPC," for European Patent Application No. 20724702.4 filed May 11, 2022 (24 pages).
"Response to Communication Pursuant to Rules 161(1) and 162 EPC," for European Patent Application No. 20724703.2 filed Jun. 8, 2022 (12 pages).
"Response to Communication Pursuant to Rules 161(1) and 162 EPC," for European Patent Application No. 20727417.6 filed Jun. 1, 2022 (8 pages).
"Response to Communication Pursuant to Rules 161(1) and 162 EPC," for European Patent Application No. 20724333.8 filed Jun. 8, 2022 (8 pages).
"Response to Final Rejection," dated Dec. 27, 2021 and Advisory Action dated Mar. 9, 2022 for U.S. Appl. No. 16/167,140, submitted via EFS-Web on Mar. 25, 2022, 11 pages.
"Response to Final Rejection," dated Feb. 1, 2022 for U.S. Appl. No. 16/855,433, submitted via EFS-Web on May 2, 2022, 9 pages.
"Response to Non-Final Rejection," dated Dec. 22, 2021 for U.S. Appl. No. 16/166,957, submitted via EFS-Web on Mar. 22, 2022, 13 pages.
"Response to Non-Final Rejection," dated Dec. 22, 2021 for U.S. Appl. No. 16/167,087, submitted via EFS-Web on Mar. 22, 2022, 9 pages.
"Response to Non-Final Rejection," dated Feb. 1, 2022 for U.S. Appl. No. 17/182,436, submitted via EFS-Web on Mar. 21, 2022, 8 pages.
"Response to Non-Final Rejection," dated Feb. 17, 2022 for U.S. Appl. No. 16/167,079, submitted via EFS-Web on May 3, 2022, 11 pages.
"Final Office Action," for U.S. Appl. No. 16/855,433 dated Feb. 1, 2022 (20 pages).
"Non-Final Office Action," for U.S. Appl. No. 16/167,079 dated Feb. 17, 2022 (37 pages).
"Non-Final Office Action," for U.S. Appl. No. 17/182,436 dated Feb. 1, 2022 (41 pages).
"Notice of Allowance," for U.S. Appl. No. 16/167,116 dated Jan. 26, 2022 (19 pages).
"Response to Final Rejection," dated Dec. 27, 2021 for U.S. Appl. No. 16/167,140, submitted via EFS-Web on Feb. 9, 2022, 9 pages.
"Response to Final Rejection," dated Nov. 15, 2021 for U.S. Appl. No. 16/850,720, submitted via EFS-Web on Feb. 11, 2022, 12 pages.
"Response to Final Rejection," dated Nov. 5, 2021 and Advisory Action dated Feb. 9, 2022 for U.S. Appl. No. 16/855,421, submitted via EFS-Web on Mar. 4, 2022.
"Communication Pursuant to Article 94(3) EPC," for European Patent Application No. 18801138.1 dated Aug. 29, 2022 (5 pages).

(56) References Cited

OTHER PUBLICATIONS

"Final Office Action," for U.S. Appl. No. 17/182,436 dated Jul. 27, 2022 (19 pages).
"International Preliminary Report on Patentability," for PCT Application No. PCT/US2021/019160 dated Sep. 9, 2022 (10 pages).
"International Search Report and Written Opinion," for PCT Application No. PCT/US2022/021161 dated Jun. 22, 2022 (15 pages).
"Non-Final Office Action," for U.S. Appl. No. 16/167,087 dated Sep. 15, 2022 (24 pages).
"Notice of Opposition," for European Patent No. 3700627 filed Aug. 24, 2022 (20 pages).
"Office Action Response," for Canadian Patent Application No. 3,079,289 filed Jul. 18, 2022 (17 pages).
"Office Action Response," for Canadian Patent Application No. 3,079,314 filed Aug. 11, 2022 (7 pages).
"Office Action," for Canadian Patent Application No. 3,079,316 dated Jun. 3, 2022 (3 pages).
"Response to Final Rejection," dated May 18, 2022 for U.S. Appl. No. 16/166,957, submitted via EFS-Web on Aug. 18, 2022, 14 pages.
"Response to Final Rejection," dated May 18, 2022 for U.S. Appl. No. 16/167,087, submitted via EFS-Web on Aug. 18, 2022, 9 pages.
"Response to Final Rejection," dated May 27, 2022 for U.S. Appl. No. 16/167,079, submitted via EFS-Web on Aug. 26, 2022, 12 pages.
"Response to Non-Final Rejection," dated Jun. 7, 2022 for U.S. Appl. No. 16/855,421, submitted via EFS-Web on Sep. 7, 2022, 9 pages.
"Response to Non-Final Rejection," dated May 27, 2022 for U.S. Appl. No. 16/167,140, submitted via EFS-Web on Aug. 25, 2022, 14 pages.
"Response to Non-Final Rejection," dated May 27, 2022 for U.S. Appl. No. 16/855,433, submitted via EFS-Web on Aug. 25, 2022, 9 pages.
"Response to Office Action," for Canadian Patent Application No. 3,079,213 filed Aug. 10, 2022 (10 pages).
"Third Office Action," for Japanese Patent Application No. 2020-542721 dated Aug. 23, 2022 (9 pages) with English translation.
Notice of Opposition for European Patent Application No. 18801134.0 on behalf of Novocure Gmbh, mailed Jun. 28, 2022 (36 pages).
"Communication Pursuant to Article 94(3) EPC," for European Patent Application No. 18800411.3 dated Dec. 22, 2022 (5 pages).
"Non-Final Office Action," for U.S. Appl. No. 16/167,140 dated Nov. 15, 2022 (29 pages).
"Non-Final Office Action," for U.S. Appl. No. 16/855,433 dated Nov. 17, 2022 (39 pages).
"Non-Final Office Action," for U.S. Appl. No. 16/855,448 dated Nov. 7, 2022 (58 pages).
"Non-Final Office Action," for U.S. Appl. No. 17/182,436 dated Nov. 23, 2022 (19 pages).
"Notice of Allowance," for U.S. Appl. No. 16/855,421 dated Nov. 16, 2022 (17 pages).
"Office Action," for Canadian Patent Application No. 3,079,213 dated Dec. 5, 2022 (4 pages).
"Office Action," for Canadian Patent Application No. 3,079,289 dated Nov. 28, 2022 (7 pages).
"Office Action," for Japanese Patent Application No. 2021-562795 dated Nov. 15, 2022 (5 pages) with English Translation.
"Office Action," for Japanese Patent Application No. 2021-562798 dated Nov. 15, 2022 (14 pages), with English translation.
"Response to Non-Final Rejection," dated Sep. 15, 2022 for U.S. Appl. No. 16/167,087, submitted via EFS-Web on Dec. 13, 2022, 8 pages.
"Response to Non-Final Rejection," dated Sep. 29, 2022 for U.S. Appl. No. 16/166,957, submitted via EFS-Web on Dec. 13, 2022, 16 pages.
"First Office Action," for Chinese Patent Application No. 201880068897.8 dated Sep. 21, 2022 (11 pages) with English Summary.
"Non-Final Office Action," for U.S. Appl. No. 16/166,957 dated Sep. 29, 2022 (41 pages).
"Response to Final Rejection," dated Jul. 22, 2022 with Request for Continued Examination, for U.S. Appl. No. 17/182,436, submitted via EFS-Web on Sep. 29, 2022, 9 pages.
"Response to Final Rejection," dated Jul. 27, 2022 for U.S. Appl. No. 17/182,436, submitted via EFS-Web on Sep. 27, 2022, 9 pages.
"Non-Final Office Action," for U.S. Appl. No. 16/850,728 dated Jan. 24, 2023 (68 pages).
"Office Action,"for Japanese Patent Application No. 2021-562797 dated Nov. 22, 2022 (9 pages), with English Translation.
"Office Action,"for Japanese Patent Application No. 2021-562966 dated Nov. 29, 2022 (8 pages) with English summary.
"Office Action,"for Japanese Patent Application No. 2021-562972 dated Nov. 8, 2022 (26 pages) with English Translation.
"Response to Communication Pursuant to Rules 161(1) and 162 EPC," for European Patent Application No. 21712639.0 filed Jan. 20, 2023 (26 pages).
"Response to Non-Final Rejection," dated Nov. 7, 2022 for U.S. Appl. No. 16/855,448, submitted via EFS-Web on Feb. 7, 2023, 9 pages.
"Communication Pursuant to Article 94(3) EPC," for European Patent Application No. 20724333.8 dated Mar. 17, 2023 (6 pages).
"Decision of Rejection," for Japanese Patent Application No. 2021-562795 dated Mar. 28, 2023 (6 pages) with English translation.
"Final Office Action," for Japanese Patent Application No. 2020-542721 dated Mar. 7, 2023 (3 pages) No Translation.
"Final Office Action," for U.S. Appl. No. 16/166,957 dated Mar. 7, 2023 (49 pages).
"Final Office Action," for U.S. Appl. No. 16/167,087 dated Mar. 6, 2023 (30 pages).
"Final Office Action," for U.S. Appl. No. 16/855,433 dated May 3, 2023 (25 pages).
"International Search Report and Written Opinion," for PCT Application No. PCT/US2023/010469 dated Apr. 12, 2023 (19 pages).
"Non-Final Office Action," for U.S. Appl. No. 16/167,079 dated Mar. 23, 2023 (40 pages).
"Notice of Allowance," for U.S. Appl. No. 16/855,448 dated Mar. 8, 2023 (19 pages).
"Response to Communication Pursuant to Article 94(3) EPC," for European Patent Application No. 18800411.3 filed May 2, 2023 (11 pages).
"Response to Communication Pursuant to Article 94(3) EPC," for European Patent Application No. 18801138.1 filed Mar. 8, 2023 (10 pages).
"Response to Non-Final Rejection," dated Jan. 24, 2023 for U.S. Appl. No. 16/850,728, submitted via EFS-Web on Apr. 20, 2023, 8 pages.
"Response to Office Action," for Canadian Patent Application No. 3,079,213 filed Mar. 8, 2023 (6 pages).
"Response to Office Action," for Canadian Patent Application No. 3,079,289 filed Mar. 24, 2023 (18 pages).
"Second Office Action," for Chinese Patent Application No. 201880068897.8 dated Feb. 27, 2023 (9 pages) with English Summary.

* cited by examiner

ELECTRICAL STIMULATION DEVICES FOR CANCER TREATMENT

This application claims the benefit of U.S. Provisional Application No. 62/837,125, filed Apr. 22, 2019, the content of which is herein incorporated by reference in its entirety.

FIELD

Embodiments herein relate to electrical stimulation devices and methods for the treatment of cancer. More specifically, the embodiments relate to electrical stimulation leads and methods that can include features related to measuring one or more electrical properties, including but not limited to impedance, capacitance, or voltage, at or near a site of a cancerous tumor.

BACKGROUND

A living organism is made up of a complex three-dimensional architecture of biological tissue including cells and extracellular matrix surrounded by intracellular and extracellular fluids. The intracellular fluid found inside of the cells of an organism is generally ionic, and includes various electrically active molecules such as ions, proteins, macronutrients, and nucleic acids. The extracellular fluid includes various fluids found outside of the cells of an organism. Examples of extracellular fluids can include the blood plasma, lymph, cerebrospinal fluid, ocular fluid, synovial fluid, and saliva, to name a few. The extracellular fluids are generally ionic in nature, and can include electrically active macronutrients such as ions, sugars, fatty acids, and metabolic waste products. The cell membranes of an organism include phospholipids and proteins, where the hydrophobic lipid tails are sandwiched between two layers of hydrophilic phosphate headgroups and various proteins associated therewith.

The biological tissue in a living organism has an electrical impedance when placed in an alternating electric field. The electrical impedance of the biological tissue of a living organism can depend on the tissue type, the health or diseased state of the tissue, and the frequency of the applied electric field. Electrical impedance of each type of biological tissue is determined by the cell type, intracellular fluid, and extracellular fluid composition for each specific tissue.

SUMMARY

In a first aspect, a medical device for treating a cancerous tumor is included. The medical device can include a first lead comprising a first wire and a second wire; a second lead comprising a third wire and a fourth wire; and a first electrode in electrical communication with the first wire, a second electrode in electrical communication with the second wire, a third electrode in electrical communication with the third wire, and a fourth electrode in electrical communication with the fourth wire. The first electrode and the third electrode can form a supply electrode pair configured to deliver one or more electric fields at or near a site of the cancerous tumor. The second electrode and the fourth electrode can form a sensing electrode pair configured to measure an impedance of the cancerous tumor independent of an impedance of the first electrode, the first wire, the third electrode, the third wire, and components in electrical communication therewith.

In a second aspect, in addition to one or more of the preceding or following aspects, or in the alternative to some aspects, the medical device can include an electric field generating circuit configured to generate the one or more electric fields.

In a third aspect, in addition to one or more of the preceding or following aspects, or in the alternative to some aspects, the first lead and the second lead are each in electrical communication with the electric field generating circuit.

In a fourth aspect, in addition to one or more of the preceding or following aspects, or in the alternative to some aspects, the medical device can include a control circuitry in communication with the electric field generating circuit, the control circuitry configured to control delivery of the one or more electric fields from the electric field generating circuit.

In a fifth aspect, in addition to one or more of the preceding or following aspects, or in the alternative to some aspects, where the control circuitry can cause the electric field generating circuit to generate one or more electric fields at frequencies selected from a range of between 10 kHz to 1 MHz at or near the site of the cancerous tumor located within a bodily tissue.

In a sixth aspect, in addition to one or more of the preceding or following aspects, or in the alternative to some aspects, where the medical device can be configured to be implanted entirely within a subject.

In a seventh aspect, in addition to one or more of the preceding or following aspects, or in the alternative to some aspects, where the medical device can be configured to be partially implanted within a subject.

In an eighth aspect, in addition to one or more of the preceding or following aspects, or in the alternative to some aspects, where the one or more electric fields are delivered to the cancerous tumor at frequencies selected from a range of from 100 kHz to 300 kHz.

In a ninth aspect, in addition to one or more of the preceding or following aspects, or in the alternative to some aspects, where a current flow through the second electrode, the second wire, the fourth electrode, the fourth wire, and components in electrical communication therewith is less than 100 pA.

In a tenth aspect, in addition to one or more of the preceding or following aspects, or in the alternative to some aspects, where the first electrode and the second electrode of the first lead are spatially separated along a longitudinal axis of the first lead by at least 1 mm; and wherein the third electrode and the fourth electrode of the second lead are spatially separated along a longitudinal axis of the second lead by at least 1 mm.

In an eleventh aspect, in addition to one or more of the preceding or following aspects, or in the alternative to some aspects, wherein the one or more electric fields comprise an electric field strength selected from a range of electric field strengths from 0.25 V/cm to 1000 V/cm.

In a twelfth aspect, a method for treating a cancerous tumor is included. The method can include implanting a first lead and a second lead at or near a site of the cancerous tumor, where the first lead includes a first wire and a second wire and the second lead includes a third wire and a fourth wire. The first wire can be in electrical communication with a first electrode; the second wire can be in electrical communication with a second electrode; the third wire can be in electrical communication with a third electrode; and the fourth wire can be in electrical communication with a fourth electrode. The first electrode and the third electrode can form a first supply electrode pair configured to deliver an electric field at or near a site of the cancerous tumor, and the second electrode and fourth electrode can form a first sensing electrode pair configured to measure impedance of the cancerous tumor independent of an impedance between the first sensing electrode pair. The method can include applying a therapeutic electric field at or near a site of the cancerous tumor using the first supply electrode pair for a predetermined period of time. The method can include measuring the impedance of the cancerous tumor using the first sensing electrode pair.

In a thirteenth aspect, in addition to one or more of the preceding or following aspects, or in the alternative to some aspects, the method can include measuring an initial impedance of the cancerous tumor prior to beginning treating the cancerous tumor, where measuring the initial impedance includes applying a diagnostic electric field at or near the site of the cancerous tumor and recording the initial impedance.

In a fourteenth aspect, in addition to one or more of the preceding or following aspects, or in the alternative to some aspects, where measuring the impedance of the cancerous tumor includes obtaining multiple measurements over a predetermined amount of time.

In a fifteenth aspect, in addition to one or more of the preceding or following aspects, or in the alternative to some aspects, the method can include determining a regression of the cancerous tumor by detecting an increase in the impedance over the predetermined period of time.

In a sixteenth aspect, in addition to one or more of the preceding or following aspects, or in the alternative to some aspects, the method can include determining a progression of the cancerous tumor by detecting a decrease in the impedance over the predetermined period of time.

In a seventeenth aspect, in addition to one or more of the preceding or following aspects, or in the alternative to some aspects, the method can include adjusting the therapeutic electric field.

In an eighteenth aspect, a medical device for treating a cancerous tumor is included. The medical device can include an electric field generating circuit configured to generate one or more electric fields and control circuitry in communication with the electric field generating circuit, where the control circuitry is configured to control delivery of the one or more electric fields from the electric field generating circuit. The control circuitry can cause the electric field generating circuit to generate one or more electric fields at frequencies selected from a range of between 10 kHz to 1 MHz at or near a site of the cancerous tumor. The medical device can include one or more supply leads in electrical communication with the electric field generating circuit, where the one or more supply leads each include one or more supply electrodes in electrical communication with the electric field generating circuit. The medical device can include one or more sensing leads in electrical communication with the control circuitry, where the one or more sensing leads can each include one or more sensing electrodes. The one or more sensing electrodes can be configured to measure an impedance of the one or more supply electrodes.

In a nineteenth aspect, in addition to one or more of the preceding or following aspects, or in the alternative to some aspects. The medical device can include a housing in which the electric field generating circuit and the control circuitry are disposed, where the housing includes a portion that is in electrical communication with the electric field generating circuit such that the housing serves as a supply electrode, and where the one or more electric fields are delivered along at least one vector including a portion of the housing serving as a supply electrode.

In a twentieth aspect, in addition to one or more of the preceding or following aspects, or in the alternative to some aspects, where the one or more sensing electrodes are configured to perform unipolar impedance measurements to differentiate the impedance of each supply electrode.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

As discussed above, the biological tissue in a living organism has an electrical impedance when placed in an alternating electric field. Like any healthy tissue, a cancerous tumor, including at least one cancerous cell population, can also exhibit an electrical impedance influenced by its cell type, intracellular fluid, and extracellular fluid associated therewith, when placed in an electric field. However, the impedance of cancerous tissue can vary in comparison to healthy tissue. Further, the impedance of cancerous tissue can vary as a result of treatment of the cancerous tissue. As such, measuring and monitoring the impedance of tissue before, during and after treatment (regardless of treatment modality) can provide valuable clinical insights in order to guide further therapy. In addition, the impedance of device components themselves (including, but not limited to, electrodes, leads, and components in electrical communication therewith) before, during and after treatment (regardless of treatment modality) can provide valuable clinical insights in order to guide further therapy.

Figure 1:
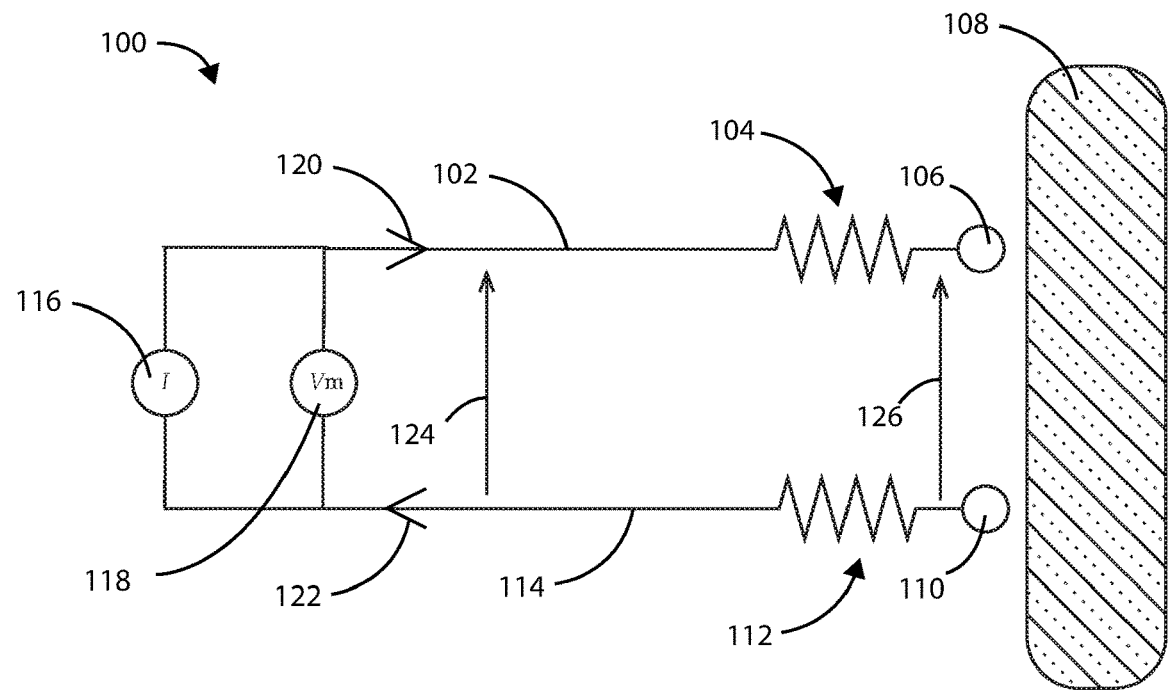
FIG. 1 is a schematic circuit diagram in accordance with various embodiments herein.

Impedance can be measured within a biological tissue using a number of methods, including a two-wire impedance measurement or a four-wire impedance measurement. Referring now to FIG. 1, a two-wire circuit diagram 100 for measuring impedance within a biological tissue is shown in accordance with the embodiments herein. The two-wire circuit diagram 100 includes a first wire 102 having a first wire resistance 104 and a first electrode 106 in electrical communication with first wire 102. The two-wire circuit diagram 100 also includes a second wire 114 having a second wire resistance 112 and a second electrode 110 in electrical communication with second wire 114. The first electrode 106 and the second electrode 110 are placed in close proximity to a tissue 108 to be treated. By way of example, the tissue 108 to be treated can include a healthy bodily tissue or a diseased bodily tissue, such as a cancerous tumor.

The two-wire circuit diagram 100 also includes a current source 116 and a voltmeter 118. The direction of the current flow through the circuit is depicted by current flow arrows 120 and 122. The first electrode 106 and the second electrode 110 are each configured to perform the functions of supplying an electric field at or near the site of the tissue 108 to be treated and to sense an impedance at or near the site of the tissue 108 to be treated. Thus, in this scenario, a known current is supplied to the tissue 108 and the voltage drop is measured using the same electrode pair (or electrical potential difference between the two electrodes of the electrode pair). Impedance can then be calculated according to Ohm's law (V=IR or V=IZ). However, when measured in this manner, the current through the circuit experiences a voltage drop across first wire resistance 104 and second wire resistance 112. The current flow through the circuit can experiences a voltage drop due to impedance within the wires, the electrodes, and any other components in electrical communication therewith. Thus, the voltage 124 measured by voltmeter 118 across the tissue 108 will include interference from the voltage drop within the components of the two-wire circuit 100 and will be different than the actual voltage drop 126 across tissue 108. As such, any impedance as measured through the tissue 108 will also include impedance of components of the two-wire circuit 100. While not intending to be bound by theory, it is believed that this interference with measuring the impedance of the tissue 108 can be detrimental to the clinical value of measurement and/or monitoring of tissue 108 impedance and make it less valuable for guiding therapy.

Figure 2:
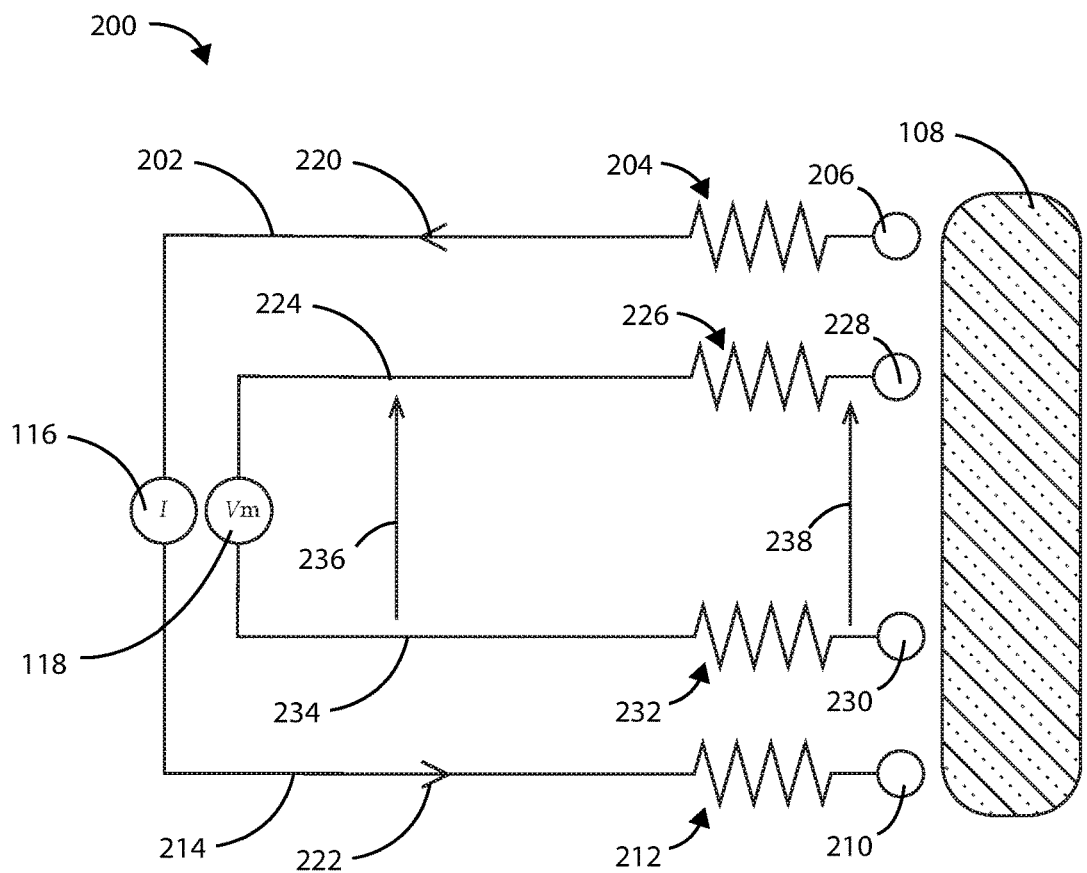
FIG. 2 is a schematic circuit diagram in accordance with various embodiments herein.

A four-wire system for measuring impedance can offer enhanced accuracy and specifically can reduce or eliminate the interference to the impedance measurement associated with a two-wire system. Referring now to FIG. 2, an exemplary four-wire circuit diagram 200 for measuring impedance within a biological tissue is shown in accordance with the embodiments herein. The four-wire circuit diagram 200 differs from the two-wire circuit diagram in that the four-wire circuit diagram includes separate supply electrodes and separate sensing electrodes. The four-wire circuit diagram 200 includes a first wire 202 having a first wire resistance 204 and a first supply electrode 206 in electrical communication with first wire 202. The four-wire circuit diagram 200 also includes a second wire 214 having a second wire resistance 212 and a second supply electrode 210 in electrical communication with second wire 214. The first supply electrode 206 and the second supply electrode 210 are placed in close proximity to a tissue 108 to be treated. By way of example, the tissue 108 to be treated can include a healthy bodily tissue or a diseased bodily tissue, such as a cancerous tumor. The first supply electrode 206 and the second supply electrode 210 are configured to supply one or more electric fields at or near the site of the tissue 108.

The four-wire circuit diagram 200 further includes a third wire 224 having a third wire resistance 226 and a first sensing electrode 228 in electrical communication with third wire 224. The four-wire circuit diagram 200 also includes a fourth wire 234 having a fourth wire resistance 232 and a second sensing electrode 230 in electrical communication with fourth wire 234. The first sensing electrode 228 and the second sensing electrode 230 are placed in close proximity to a tissue 108 to be treated, and they are configured to measure an impedance within the tissue 108.

The four-wire circuit diagram 200 also includes a current source 116 and a voltmeter 118. The direction of the current flow through the circuit is depicted by current flow arrows 220 and 222. The current is configured to flow through the first supply electrode 206, the tissue 108, and the second supply electrode 210, and any wires and components in electrical communication therewith. In contrast to the two-wire circuit 100, the four-wire circuit 200 is configured such that negligible current flows through the sensing electrodes and the wires and components in electrical communication therewith. As such, the voltage 236 measured by the voltmeter 118 is substantially identical to the voltage 238 across the tissue 108. Any impedance within the first wire, the first supply electrode, the second wire, the second supply electrode, and any components in electrical communication therewith will not be measured along with the impedance sensed across the tissue 108 alone.

Figure 3:
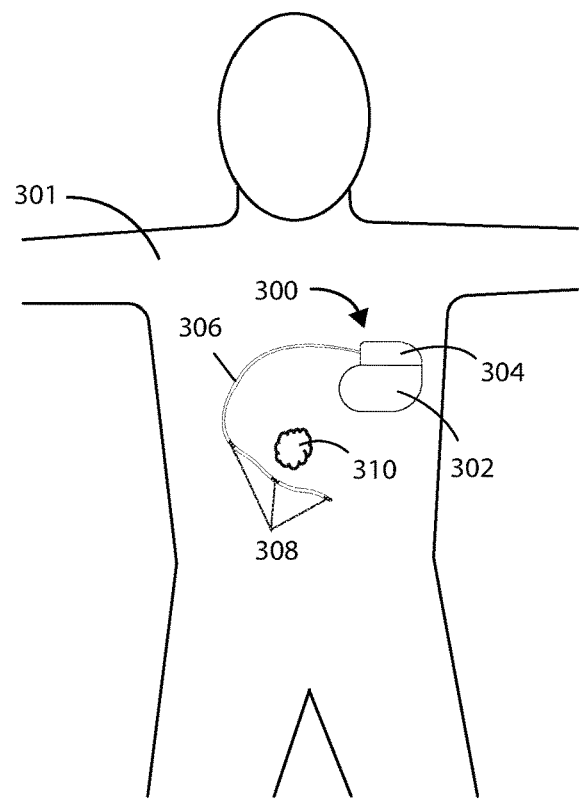
FIG. 3 is a schematic view a medical device in accordance with various embodiments herein.
Figure 4:
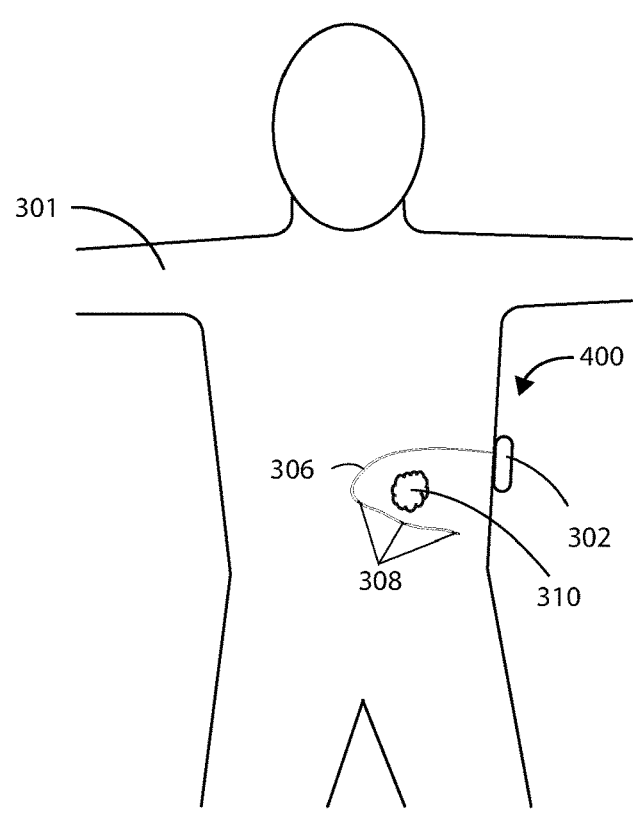
FIG. 4 is a schematic view a medical device in accordance with various embodiments herein.

The impedance of a cancerous tumor can be measured using any of the medical devices described herein and can be done using a two-wire, four-wire, or other system. Referring now to FIG. 3 and FIG. 4, schematic diagrams of a subject 301 with a cancerous tumor 310 are shown in accordance to the embodiments herein. In FIG. 3, the subject 301 has a medical device 300 implanted entirely within the body of the subject 301 at or near the site of cancerous tumor 310. Various implant sites can be used including areas such as in the limbs, the upper torso, the abdominal area, the head, and the like. In FIG. 4, the subject 301 has a medical device 400 at least partially implanted within body of the subject 301 at or near the site of a cancerous tumor. In some embodiments, the medical device can be entirely external to the subject. In some embodiments, the medical device can be partially external to the subject. In some embodiments, the medical device can be partially implanted and partially external to the body of a subject. In other embodiments, a partially implanted medical device can include a transcutaneous connection between components disposed internal to the body and external to the body. A partially or fully implanted medical device can wirelessly communicate with a partially or fully external portion of a medical device over a wireless connection.

In some embodiments, a portion of the medical device can be entirely implanted and a portion of the medical device can be entirely external. For example, in some embodiments, one or more electrodes or leads can be entirely implanted within the body, whereas the portion of the medical device that generates an electric field, such as an electric field generator, can be entirely external to the body. It will be appreciated that in some embodiments described herein, the electric field generators described can include the many of the same components as and can be configured to perform many of the same functions as a pulse generator. In embodiments where a portion of a medical device is entirely implanted, and a portion of the medical device is entirely external, the portion of the medical device that is entirely external can communicate wirelessly with the portion of the medical device that is entirely internal. However, in other embodiments a wired connection can be used.

The medical device 300 can include a housing 302 and a header 304 coupled to the housing 302, and medical device 400 can include a housing 302. Various materials can be used. However, in some embodiments, the housing 302 can be formed of a material such as a metal, ceramic, polymer, composite, or the like. In some embodiments, the housing 302, or one or more portions thereof, can be formed of titanium. The header 304 can be formed of various materials, but in some embodiments the header 304 can be formed of a translucent polymer such as an epoxy material. In some embodiments the header 304 can be hollow. In other embodiments the header 304 can be filled with components and/or structural materials such as epoxy or another material such that it is non-hollow.

In some embodiments where a portion of the medical device 300 or 400 is partially external, the header 304 and housing 302 can be surrounded by a protective casing made of durable polymeric material. In other embodiments, where a portion of the medical device 300 or 400 is partially external, the header 304 and housing 302 can be surrounded by a protective casing made of a combination of polymeric material, metallic material, and/or glass material.

Header 304 can be coupled to one or more leads, such as leads 306. The header 304 can serve to provide fixation of the proximal end of one or more leads 306 and electrically couple the one or more leads 306 to one or more components within the housing 302. The one or more leads 306 can include one or more electrodes, such as electrodes 308, disposed along the length of the leads 306. In some embodiments, electrodes 308 can include electric field generating electrodes, also referred to herein as "supply electrodes," and in other embodiments electrodes 308 can include electric field sensing electrodes. In some embodiments, leads 306 can include both electric field generating and electric field sensing electrodes. In other embodiments, leads 306 can include any number of electrodes that are both electric field sensing and electric field generating. It will be appreciated that while many embodiments of medical devices herein are designed to function with leads, leadless medical devices that generate electrical fields are also contemplated herein. In some embodiments, the electrodes 308 can be tip electrodes on the most distal end of the leads 306.

Figure 5:
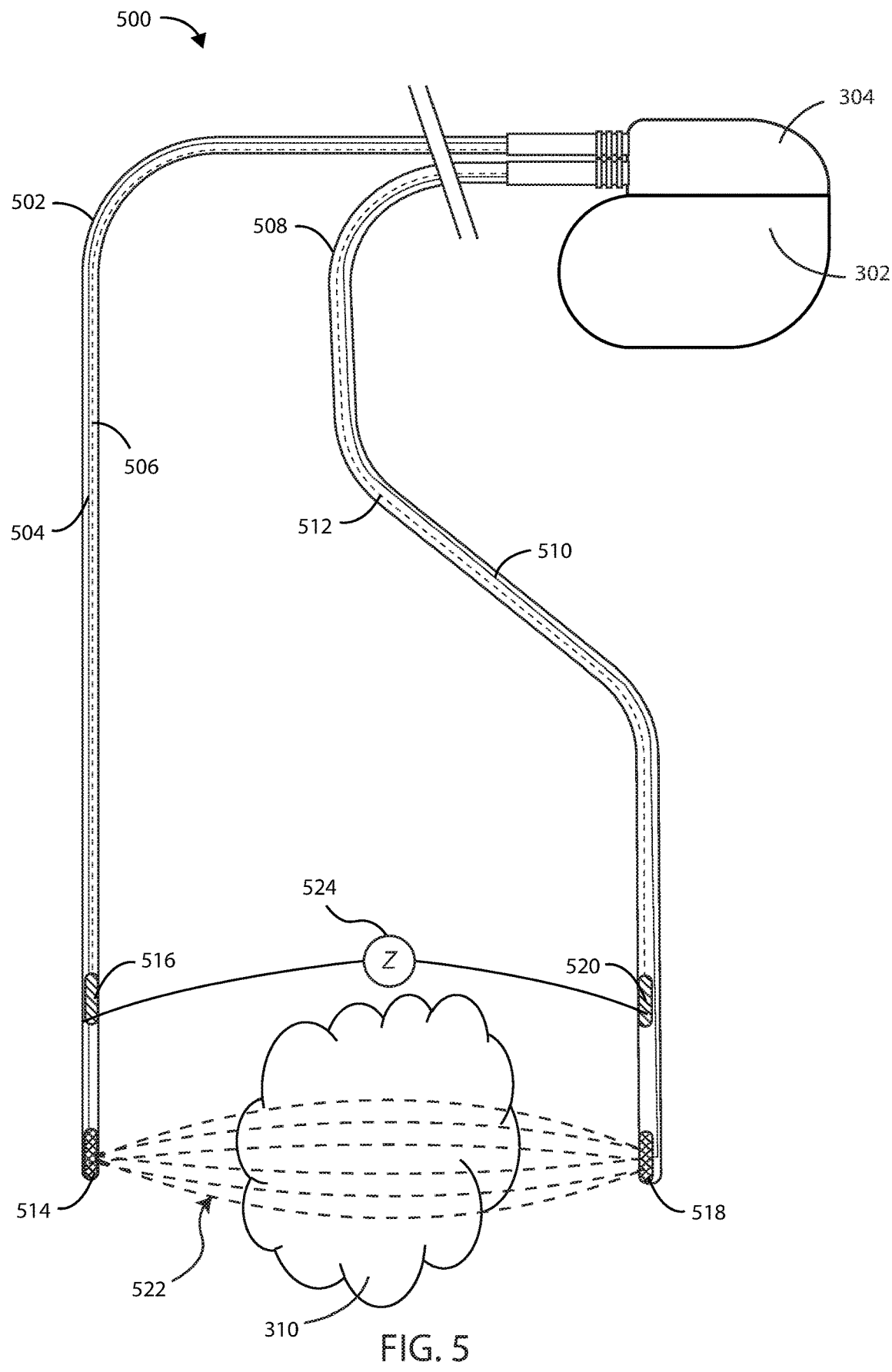
FIG. 5 is a schematic view a medical device in accordance with various embodiments herein.

It will be appreciated that components within a medical device, including leads, electrodes, and any components in electrical communication with any of the forgoing that form part of an electrical circuit can produce an impedance within the medical device. A medical device having four wires and four electrodes can be configured to measure impedance within a cancerous tumor and can separate the impedance of the medical device components from the impedance across the cancerous tumor, thus allowing a more accurate measurement of impedance associate with the cancerous tumor itself. Referring now to FIG. 5, a medical device 500 for treating a cancerous tumor 310 is shown in accordance with the embodiments herein. The medical device 500 can include a first lead 502 comprising a first wire 504 (shown as a solid line) and a second wire 506 (shown as a dashed line). The medical device 500 can include a second lead 508 comprising a third wire 510 (shown as a solid line) and a fourth wire 512 (shown as a dashed line). The first wire 504 and the third wire 510 can be configured as supply wires for supplying an electric field at or near the site of the cancerous tumor. The second wire 506 and the fourth wire 512 can be configured as sensing wires for measuring an impedance at or near the site of the cancerous tumor.

The first lead 502 of medical device 500 can include a first electrode 514 in electrical communication with the first wire 504 and a second electrode 516 in electrical communication with the second wire 506. The second lead 508 of medical device 500 can include a third electrode 518 in electrical communication with the third wire 510 and a fourth electrode 520 in electrical communication with the fourth wire 512. The first electrode 514 and the third electrode 518 can be configured as supply electrodes to form a supply electrode pair that can deliver an electric field 522 at or near a site of the cancerous tumor 310. The second electrode 516 and the fourth electrode 520 can be configured as electric field sensing electrodes to form a sensing electrode pair configured to measure an impedance 524 of the cancerous tumor 310, where impedance 524 is independent of an impedance of any circuit formed by the first electrode 514, the first wire 504, the third electrode 518, the third wire 510, and any components in electrical communication therewith.

In some embodiments, if two or more electrodes are present on the leads of the medical devices herein, each electrode can be spatially separated along a longitudinal axis of the lead by at least 0.1, 0.2, 0.25, 0.3, 0.35, 0.4, 0.5, 0.75, 1, 2, 3, 4, 5, or 10 cm (or by an amount falling within a range between any of the foregoing). By way of example, the first electrode 514 and the 516 second electrode of the first lead 502 are spatially separated along a longitudinal axis of the first lead 502 by at least 1 mm; and the third electrode 518 and the fourth electrode 520 of the second lead 508 are spatially separated along a longitudinal axis of the second lead 508 by at least 1 mm.

In some embodiments, the electrodes described herein can be spatially separated along a longitudinal axis of the leads described herein by a distance that can be greater than or equal 1 mm, 5 mm, 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, or 100 mm, 150 mm, 200 mm, or 250 mm. In some embodiments, the electrodes herein can be spatially separated in more than one dimension from neighboring electrodes by a distance that can be greater than or equal 1 mm, 5 mm, 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, or 100 mm, 150 mm, 200 mm, or 250 mm.

It will be appreciated that the current flow through the first electrode 514 and third electrode 518 will not appreciably pass through the sensing electrode pair, including the second electrode 516 and fourth electrode 520. Thus, the current flow through the second electrode 516, the second wire 506, the fourth electrode 520, the fourth wire 512, and components in electrical communication therewith is negligible. In some embodiments, the current flow through the second electrode 516, the second wire 506, the fourth electrode 520, the fourth wire 512, and components in electrical communication therewith is less than 2000, 1000, 750, 500, 250, 100, 50, or 10 pA.

Figure 6:
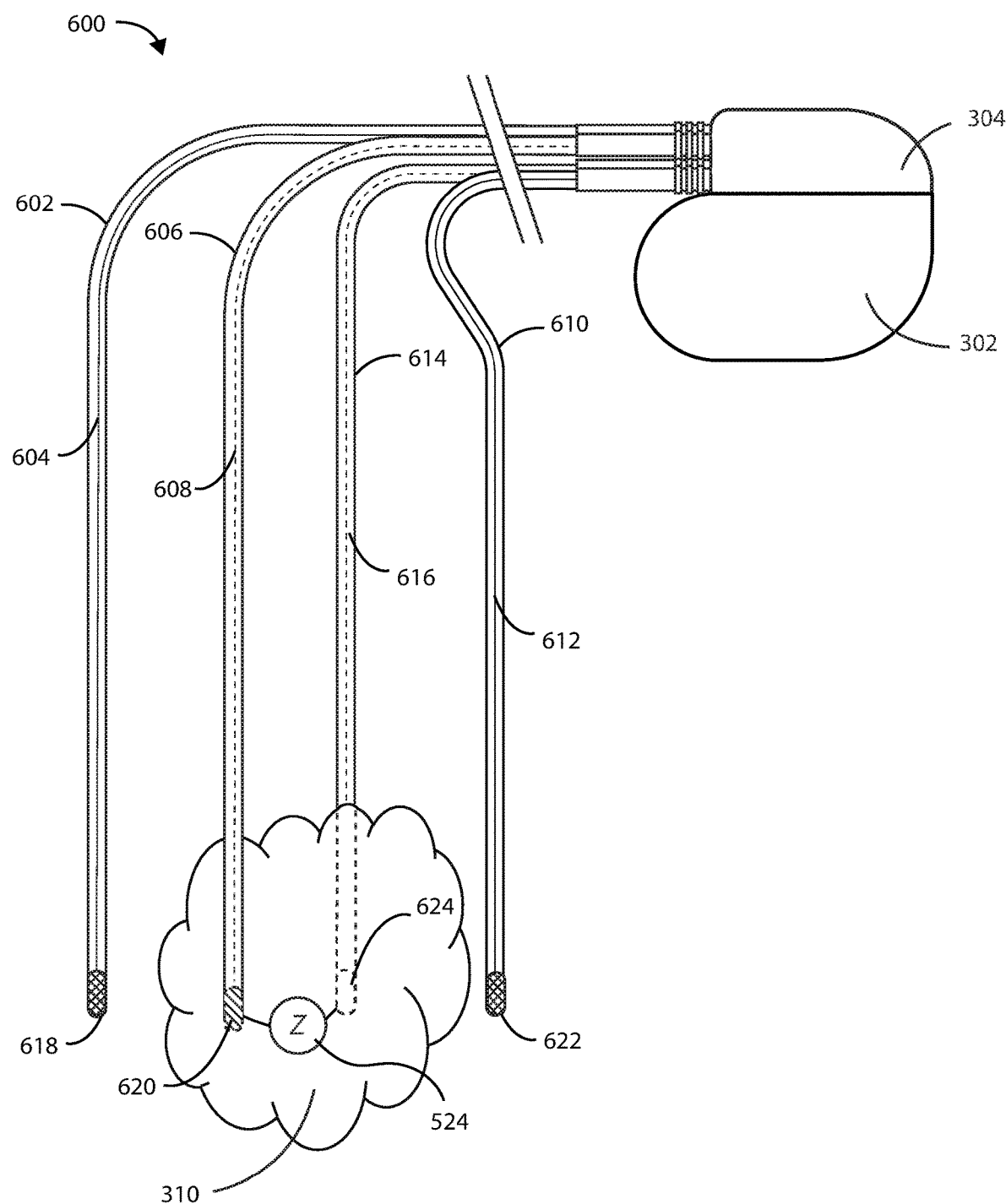
FIG. 6 is a schematic view a medical device in accordance with various embodiments herein.

In some embodiments, the four wires of the medical devices herein can each be present in separate leads, spatially separate from one another. Referring now to FIG. 6, medical device 600 for treating a cancerous tumor 310 is shown in accordance with the embodiments herein. The medical device 600 can include a first lead 602 comprising a first wire 604, a second lead 606 comprising a second wire 608, a third lead 610 comprising a third wire 612, and a fourth lead 614 comprising a fourth wire 616. The first wire 604 and the third wire 612 can be configured as supply wires for supplying an electric field at or near the site of the cancerous tumor. The second wire 608 and the fourth wire 616 can be configured as sensing wires for measuring an impedance at or near the site of the cancerous tumor.

The first lead 602 can include a first electrode 618 in electrical communication with the first wire 604. The second lead 606 can include a second electrode 620 in electrical communication with the second wire 608. The third lead 610 can include a third electrode 622 in electrical communication with the third wire 612. The fourth lead 614 can include a fourth electrode 624 in electrical communication with the fourth wire 616. The first electrode 618 and the third electrode 622 can be configured as supply electrodes to form a supply electrode pair configured to deliver an electric field at or near a site of the cancerous tumor 310. The second electrode 620 and the fourth electrode 624 can be configured as sensing electrodes to form a sensing electrode pair configured to measure impedance 524 of the cancerous tumor 310, where the impedance 524 is independent of an impedance of the first electrode 618, the first wire 604, the third electrode 622, the third wire 612, and any components in electrical communication therewith. In some embodiments, the first wire, the second wire, the third wire, the fourth wire, etc., can be electrically insulated from one another. In other embodiments, more than four leads and/or more than four wires can be utilized.

The first electrode 618 and the third electrode 622 that form the supply electrode pair can deliver an electric field along a first vector at or near the site of a cancerous tumor, and the second electrode 620 and the fourth electrode 624 that form the sensing electrode pair can measure impedance 524 of the cancerous tumor along a second vector at or near the site of the cancerous tumor. The first vector and second vector can be spatially and or directionally separate from one another. In some embodiments, the first vector and second vector can be spatially and or directionally separated (e.g., the vectors can be disposed at an angle with respect to one another) by at least about 10, 20, 30, 40, 50, 60, 70, 80 or 90 degrees. It will be appreciated that the supply electrode pair can deliver an electric field at or near the site of a cancerous tumor along multiple vectors, and that the sensing electrode pair can similarly measure impedance along multiple vectors that are spatially separate from the vector used to deliver the electric field. In some embodiments, the sensing electrodes can be configured to sense an impedance 524 within a cancerous tumor along one or more vectors that are non-therapy vectors.

Figure 7:
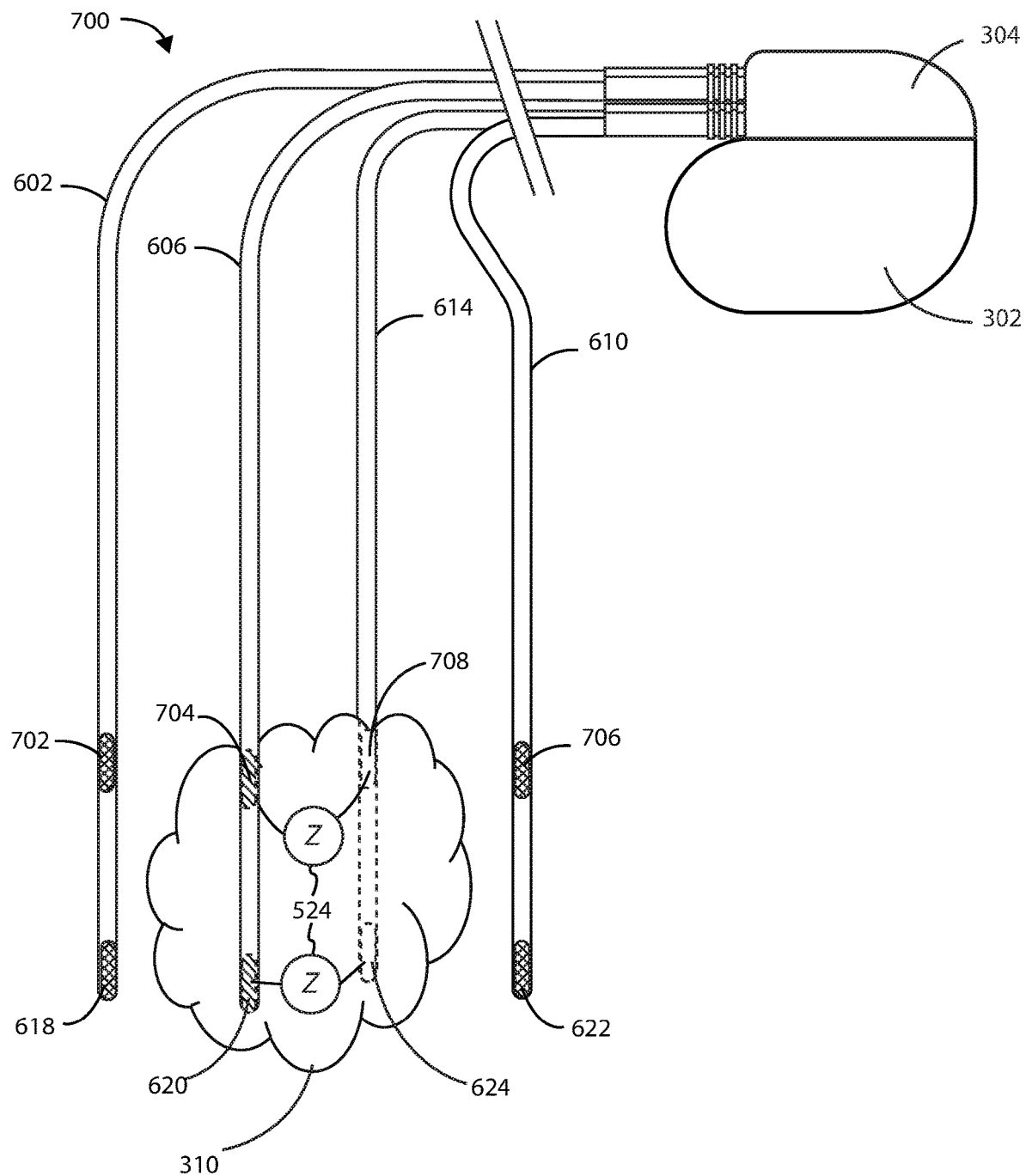
FIG. 7 is a schematic view a medical device in accordance with various embodiments herein.

The medical devices herein can include additional configurations using more than one set of four wires to measure impedance at or near the site of a cancerous tumor. For example, the medical devices herein can include two sets of four wires to measure impedance within a cancerous tumor. Referring now to FIG. 7, medical device 700 for treating a cancerous tumor 310 is shown in accordance with the embodiments herein. Medical device 700 includes a first lead 602, a second lead 606, a third lead 610, and a fourth lead 614. The first lead 602 can include a first electrode 618 and a fifth electrode 702. The second lead 606 can include a second electrode 620 and a sixth electrode 704. The third lead 610 can include a third electrode 622 and a seventh electrode 706. The fourth lead 614 can include a fourth electrode 624 and an eighth electrode 708. It will be appreciated that, while not shown, the fifth electrode is in electrical communication with a fifth wire, the sixth electrode is in electrical communication with a sixth wire, the seventh electrode is in electrical communication with a seventh wire, and the eighth electrode is in electrical communication with an eighth wire. Each of the wires within each respective lead can be electrically insulated from each other.

The first electrode 618 and the third electrode 622 can be configured as supply electrodes that form a first supply electrode pair configured to deliver an electric field at or near a site of the cancerous tumor 310. The second electrode 620 and the fourth electrode 624 can be configured as sensing electrodes that form a first sensing electrode pair configured to measure an impedance 524 of the cancerous tumor 310, where impedance 524 is independent of an impedance of the first electrode 618, the third electrode 622, and any wires and any components in electrical communication therewith. The fifth electrode 702 and the seventh electrode 706 can be configured as supply electrodes that form a second supply electrode pair configured to deliver an electric field at or near a site of the cancerous tumor 310. The sixth electrode 704 and the eighth electrode 708 can be configured as sensing electrodes that form a second sensing electrode pair configured to measure an impedance 524 of the cancerous tumor 310, where impedance 524 is independent of an impedance of the fifth electrode 702, seventh electrode 706, and any wires and any components in electrical communication therewith.

The first electrode 618 and the third electrode 622 that form the first supply electrode pair can deliver an electric field along a first vector at or near the site of a cancerous tumor, and the second electrode 620 and the fourth electrode 624 that form the first sensing electrode pair can measure an impedance 524 along a second vector at or near the site of a cancerous tumor. The fifth electrode 702 and the seventh electrode 706 that form the second supply electrode pair can deliver an electric field along a third vector at or near the site of a cancerous tumor, and the sixth electrode 704 and the eighth electrode 708 that form the second sensing electrode pair can measure an impedance 524 along a fourth vector at or near the site of a cancerous tumor.

The electric field can be delivered by the first supply electrode pair at or near the site of a cancerous tumor along a first vector, while the first sensing electrode pair can sense impedance along a second vector that is spatially and/or directionally separate from the first vector. In some embodiments, the first vector and second vector can be spatially and/or directionally separated (e.g., the vectors can be disposed at an angle with respect to one another) by at least about 10, 20, 30, 40, 50, 60, 70, 80 or 90 degrees. Similarly, the electric field can be delivered by the second supply electrode pair at or near the site of a cancerous tumor along a third vector, while the second sensing electrode pair can sense impedance along a fourth vector that is spatially separate from the third vector. In some embodiments, the third vector and fourth vector can be spatially and/or directionally separated (e.g., the vectors can be disposed at an angle with respect to one another) by at least about 10, 20, 30, 40, 50, 60, 70, 80 or 90 degrees. It will be appreciated that the first or second supply electrode pairs can deliver an electric field at or near the site of a cancerous tumor along multiple vectors, and that the first or second sensing electrode pairs can similarly measure impedance along multiple vectors that are spatially and/or directionally separate from the vector used to deliver the electric field.

It will be appreciated that while the first and second supply electrode pairs of medical device 700 are disposed across the first lead 602 and third lead 610, and the first and second sensing electrode pairs are found disposed across the second lead 606 and fourth lead 614, any configuration of electrode pairs can be implemented on the leads of the medical devices herein. By way of example, in FIG. 7, first lead 602 and third lead 610 can each include a first supply electrode pair and a first sensing electrode pair, and second lead 606 and fourth lead 614 can also include a first supply electrode pair and a first sensing electrode pair.

Figure 8:
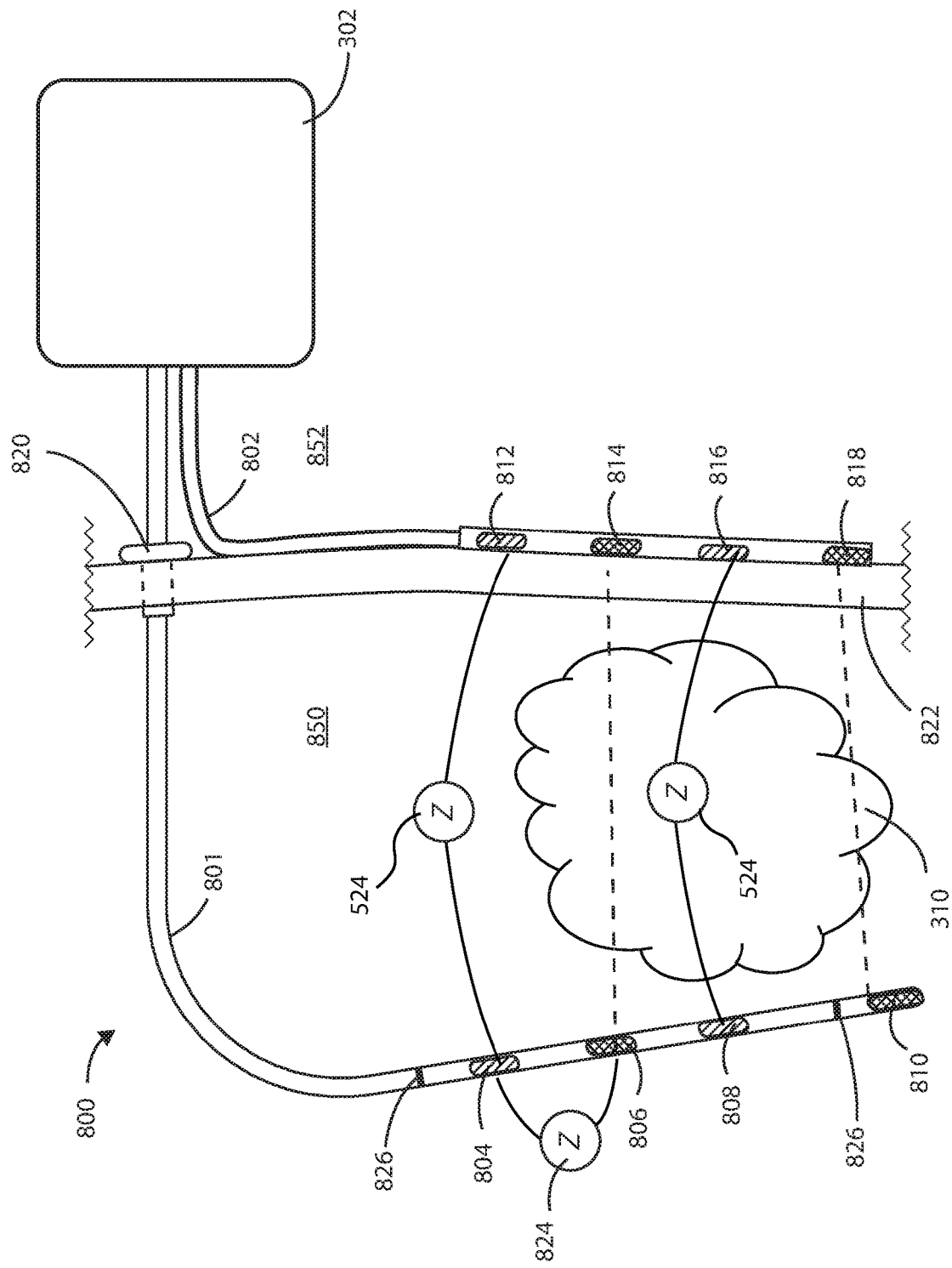
FIG. 8 is a schematic view a medical device in accordance with various embodiments herein.

In some embodiments herein, the medical devices can include both internal and external components. Referring now to FIG. 8, a schematic diagram of a medical device 800 is shown in accordance with the embodiments herein. Medical device 800 can include an internal portion at the internal side 850 of the subject's body and an external portion at the external side 852 of the subject's body. The internal portion of medical device 800 can include internal electric lead 801 and the external portion can include the housing 302 and the external electric lead 802. The medical device 800 can also include a transcutaneous access port 820 spanning the exterior surface 822 of the subjects body at or near the site of the cancerous tumor suitable to receive one or more leads or catheters. By way of example, transcutaneous access port 820 can be configured to receive at least one of the internal electric lead 801, a drug delivery catheter for delivery of one or more chemotherapeutic agents, an optical lead comprising one or more optical emitters for delivering optical energy, a biopsy apparatus for obtaining a biopsy sample from the cancerous tumor, or an irrigation catheter for flushing the site of the cancerous tumor of waste products or bodily fluids.

Internal electric lead 801 can include one or more electrodes such as sensing electrodes 804 and 808, and supply electrodes 806 and 810 disposed along the length of internal electric lead 801. External electric lead 802 can include sensing electrodes 812 and 816, and supply electrodes 814 and 818 disposed along the length of the external electric lead 802. In some embodiments, electrodes 804, 806, 808, 810, 812, 814, 816, and 818 can include any configuration of electric field generating electrodes (i.e., supply electrodes) and electric field sensing electrodes. In some embodiments, internal electric lead 801 or external electric lead 802 can include both electric field generating and electric field sensing electrodes in any configuration.

The proximal ends of internal electric lead 801 or external electric lead 802 are disposed within the housing 302. The distal ends of internal electric lead 801 can surround a cancerous tumor 310 such that the electrodes 804, 806, 808, and 810 are brought into proximity of the cancerous tumor 310. External electric lead 802 can be placed on the exterior of the subject's body near the site of the cancerous tumor such that the electrodes 812, 814, 816, and 818 are in electrical communication with electrodes 804, 806, 808, and 810 on internal electric lead 801. In some embodiments, the internal electric lead 801 can be positioned within the vasculature such that electrodes 804, 806, 808, and 810 are adjacent to or positioned within the cancerous tumor 310. However, it will be appreciated that internal electric lead 801 can be disposed in various places within or around the cancerous tumor 310. In some embodiments, the internal electric lead 801 can pass directly through the cancerous tumor 310.

In some embodiments, the internal electric lead 801 can include one or more tracking markers 826 along the length of the internal electric lead 801 for use in determining the precise location of the electrodes relative to the tumor. In some embodiments, the one or more tracking markers can be disposed directly distal or directly proximal to the one or more electrodes disposed on the internal electric lead 801. In some embodiments, the tracking markers can be formed from a magnetic material. In some embodiments, the tracking markers can be formed from a radiographic material. In some embodiments, the tracking markers can be formed from a fluorographic material.

It will be appreciated that a plurality of electric field vectors can be generated between various combinations of supply electrodes 806, 810, 814, or 818 disposed along internal electric lead 801 and external electric lead 802 to create an electric field. For example, one or more electric field vectors can be generated between supply electrodes 806 and 814. Similarly, one or more electric field vectors can be generated between supply electrodes 810 and 818. It will also be appreciated that one or more electric field vectors can be generated between any combination of supply electrodes 806, 810, 814, or 818. In some embodiments, one or more electric field vectors can be generated between any combination of supply electrodes 806, 810, 814, or 818 and the housing 302 of medical device 800.

It will be appreciated that sensing electrodes 804, 808, 812, and 816 can sense an impedance 524 within the cancerous tumor 310 along one or more vectors between any combination of sensing electrodes 804, 808, 812, and 816, where sensing an impedance 524 of a cancerous tumor can be independent of any impedance present in any of supply electrodes 806, 810, 814, or 818 or any wires or components in electrical communication therewith. Each sensing electrode can be configured to measure impedance of the cancerous tumor 310 independent of an impedance produced by any of the supply electrodes, leads, wires and any components in electrical communication therewith.

It will be appreciated that sensing electrodes 804, 808, 812, and 816 can sense an impedance 824 of any of the supply electrodes along one or more vectors between any combination of sensing electrodes 804, 808, 812, and 816 and the supply electrodes 806, 810, 814, or 818. In some embodiments, the electrodes 804, 808, 812, and 816 can be sensing electrodes that can sense an impedance 824 of any of the supply electrodes along one or more non-therapy vectors. Each sensing electrode can be further configured to measure impedance of any of the electrodes 806, 810, 814, or 818, which can be supply electrodes, where the measured impedance is independent of an impedance produced by any of the other supply electrodes, leads, wires and any components in electrical communication therewith. In some embodiments, the supply electrodes 806, 810, 814, or 818 can perform unipolar impedance measurements to differentiate the impedance of each supply electrode. A "unipolar" impedance measurement refers to the scenario where the housing (or case or can) of the implanted device itself serves as one of the two electrodes in the pair required for passing a current in order to measure voltage drop and derive impedance. A "bipolar" impedance measurement refers to the scenario where the housing (or case or can) of the implanted device itself does not serve as one of the two electrodes in the pair required for passing a current in order to measure voltage drop and derive impedance (e.g., the two electrodes are disposed on leads or other structures external to the housing of implanted device). In some embodiments, the various impedance measurements herein can be unipolar impedance measurements, while in other embodiments the various impedance measurements herein can be bipolar impedance measurements.

Figure 9:
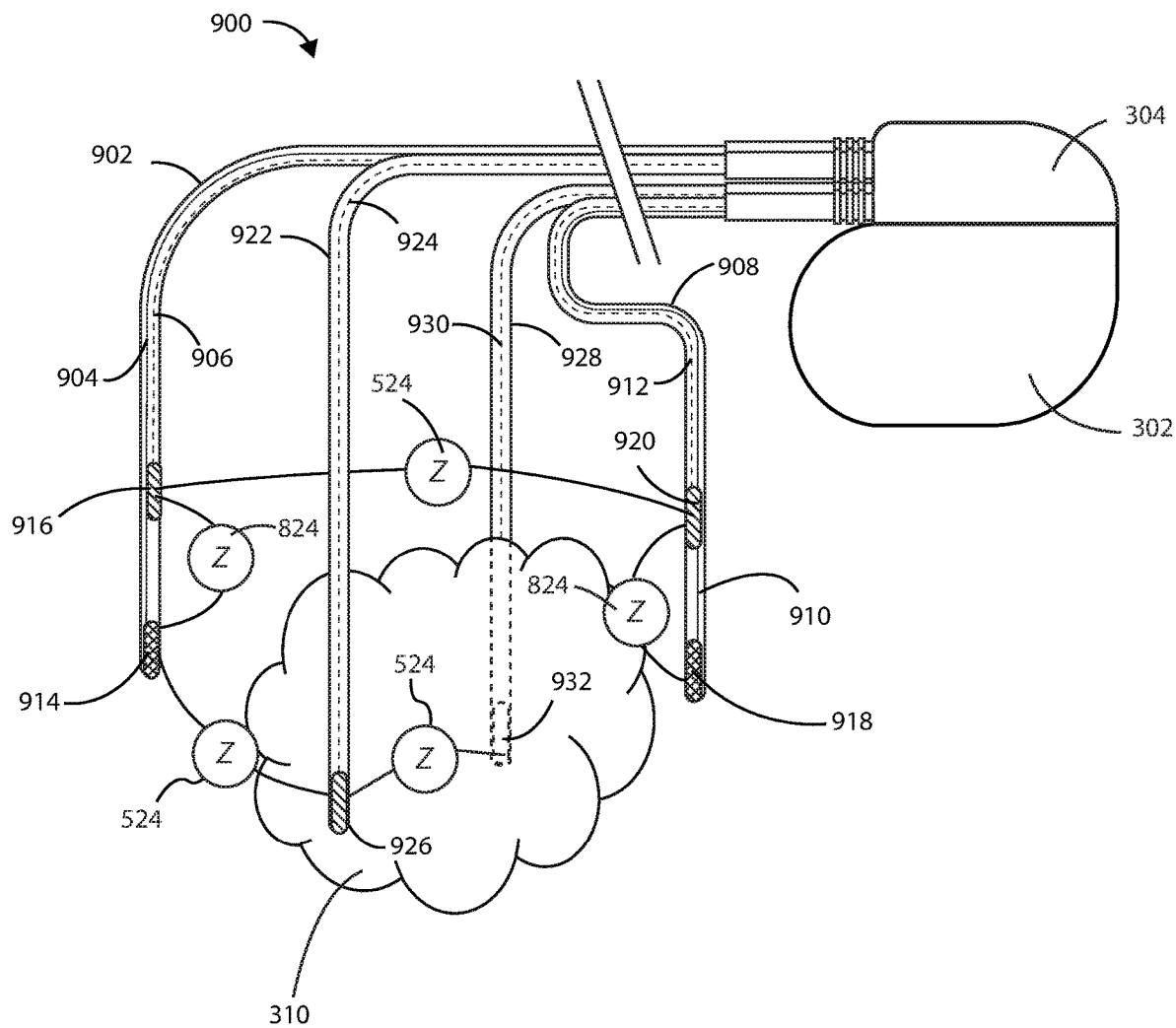
FIG. 9 is a schematic view a medical device in accordance with various embodiments herein.

The medical devices described herein for treating a cancerous tumor can also include one or more sensing electrodes that can be configured to measure an impedance of one or more supply electrodes to monitor the quality of the electrode during a given therapy. Referring now to FIG. 9, a medical device 900 is shown in accordance with the embodiments herein. Medical device 900 can include an electric field generating circuit configured to generate one or more electric fields at or near the site of a cancerous tumor 310. The medical device 900 can include control circuitry in communication with the electric field generating circuit, the control circuitry configured to control delivery of the one or more electric fields from the electric field generating circuit. The control circuitry can cause the electric field generating circuit to generate one or more electric fields at frequencies selected from a range of between 10 kHz to 1 MHz at or near a site of the cancerous tumor.

The medical device 900 can include one or more supply leads in electrical communication with the electric field generating circuit, the one or more supply leads can each include one or more supply electrodes in electrical communication with the electric field generating circuit. The medical device 900 can also include one or more sensing leads in electrical communication with the control circuitry, the one or more sensing leads can each one or more sensing electrodes. In some embodiments, the leads herein can include a combination lead that can serve either as a supply lead to provide an electric field at or near the site of a cancerous tumor, a sensing lead to measure an impedance of either a cancerous tumor, a healthy tissue, or a supply electrode, or both a supply and sensing lead where indicated.

Medical device 900 includes first lead 902, second lead 908, third lead 922, and fourth lead 928. The first lead 902 of medical device 900 can include a first electrode 914 in electrical communication with a first wire 904 and a second electrode 916 in electrical communication with a second wire 906. The second lead 908 of medical device 900 can include a third electrode 918 in electrical communication with the third wire 910 and a fourth electrode 920 in electrical communication with the fourth wire 912. The first electrode 914 and the third electrode 918 can be configured as supply electrodes to form a supply electrode pair that can deliver an electric field at or near a site of the cancerous tumor 310. The second electrode 916 and the fourth electrode 920 can be configured as sensing electrodes to form a sensing electrode pair configured to measure an impedance 524 of the cancerous tumor 310 independent of an impedance of a circuit formed by the first electrode 914, the first wire 904, the third electrode 918, the third wire 910, and any components in electrical communication therewith. The second electrode 916 and the fourth electrode 920 can be configured as sensing electrodes that can individually, or together as a pair, measure an impedance 824 of any of the supply electrodes 914 or 918, where an impedance 824 of any of the supply electrodes is independent of an impedance of a circuit formed by the first electrode 914, the first wire 904, the third electrode 918, the third wire 910, and any components in electrical communication therewith.

The third lead 922 can include a fifth electrode 926 in electrical communication with a fifth wire 924, and the fourth lead 928 can include a sixth electrode 932 in electrical communication with a fifth wire 930. The fifth electrode 926 and the sixth electrode 932 can be configured as sensing electrodes that form a sensing electrode pair configured to measure an impedance 524 of the cancerous tumor, where impedance 524 is independent of an impedance of a circuit formed by the first electrode 914, the first wire 904, the third electrode 918, the third wire 910, and any components in electrical communication therewith. The fifth electrode 926 and the sixth electrode 932 can be configured as sensing electrodes to measure impedance 824 of the one or more supply electrodes, where impedance 824 of any of the supply electrodes is independent of an impedance of a circuit formed by the first electrode 914, the first wire 904, the third electrode 918, the third wire 910, and any components in electrical communication therewith. In some embodiments, the sensing electrodes 926 and 932 can perform unipolar impedance measurements to differentiate the impedance of each supply electrode.

In some embodiments, an increase in the impedance of one or more supply electrodes can indicate a broken or failing electrode. In some embodiments, if a supply electrode is determined to be broken or failing, the housing 302 of medical device 900 can be used as a supply electrode. The housing 302 can include a portion that is in electrical communication with the electric field generating circuit, such that the housing 302 can serve as a supply electrode. The one or more electric fields can be delivered along at least one vector including a portion of the housing serving as a supply electrode.

It will be appreciated that medical device 900 can include an electric field generating circuit configured to generate one or more electric fields along a first vector, wherein the first vector can include a non-therapy vector. The medical device 900 can also include control circuitry in communication with the electric field generating circuit, where the control circuitry is configured to control delivery of one or more electric fields from the electric field generating circuit. Electric field generating circuits and control circuitry will be discussed in more detail elsewhere herein. The control circuitry can cause the electric field generating circuit to generate one or more electric fields at frequencies selected from a range of between 10 kHz to 1 MHz at a site of the cancerous tumor.

One or more supply leads of medical device 900 can be in electrical communication with the electric field generating circuit, where the one or more supply leads each can each include one or more supply electrodes in electrical communication with the electric field generating circuit. One or more sensing leads of medical device 900 can be in electrical communication with the control circuitry, where the one or more sensing leads can each include one or more sensing electrodes. The one or more sensing electrodes can be configured to measure an impedance change in the one or more supply electrodes along a second vector that is different than the first vector along which the one or more electric fields are delivered to the cancerous tumor. In some embodiments, the one or more sensing electrodes of medical device 900 can be configured to measure an impedance change in the cancerous tumor along a second vector that is different than the first vector along which the one or more electric fields are delivered to the cancerous tumor.

In some embodiments, the medical device 900 can include a housing 302 in which the electric field generating circuit and the control circuitry are disposed, where the housing includes a portion that is in electrical communication with the electric field generating circuit to serve as a supply electrode. The one or more electric fields can be delivered along at least one vector including a portion of the housing serving as a supply electrode. In some embodiments of medical device 900, one or more sensing electrodes can be configured to perform unipolar impedance measurements to differentiate the impedance of each supply electrode. In some embodiments of medical device 900, each supply electrode and each sensing electrode is spatially separated along a longitudinal axis of the one or more leads by at least 0.1, 0.2, 0.25, 0.3, 0.35, 0.4, 0.5, 0.75, 1, 2, 3, 4, 5, or 10 cm (or by an amount falling within a range between any of the foregoing).

In some embodiments, the electrodes described herein can be spatially separated along a longitudinal axis of the leads described herein by a distance that can be greater than or equal 1 mm, 5 mm, 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, or 100 mm, 150 mm, 200 mm, or 250 mm. In some embodiments, the electrodes herein can be spatially separated in more than one dimension from neighboring electrodes by a distance that can be greater than or equal 1 mm, 5 mm, 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, or 100 mm, 150 mm, 200 mm, or 250 mm.

In some embodiments of medical device 900, measuring an impedance change in one or more supply electrodes along a second vector comprises measuring the impedance change along a second vector that is spatially separate from the first vector along which the one or more electric fields are delivered to the cancerous tumor by at least 30 degrees, by at least 60 degrees, or by at least 90 degrees. In some embodiments, the first vector and second vector can be spatially separated (e.g., the vectors can be disposed at an angle with respect to one another) by at least about 10, 20, 30, 40, 50, 60, 70, 80 or 90 degrees. It will be appreciated that the supply electrode pair can deliver an electric field at or near the site of a cancerous tumor along multiple vectors, and that the sensing electrode pair can similarly measure impedance along multiple vectors that are spatially separate from the vector used to deliver the electric field.

The various medical devices herein can include additional components in one or more configurations. The medical devices can include an electric field generating circuit configured to generate one or more electric fields at or near the site of the cancerous tumor. The leads of the medical devices, such as a first lead, a second lead, a third lead, a fourth lead, etc., can each be in electrical communication with the electric field generating circuit. The medical devices can also include control circuitry in communication with the electric field generating circuit, where the control circuitry can be configured to control delivery of one or more electric fields from the electric field generating circuit. The control circuitry can cause the electric field generating circuit to generate one or more electric fields at frequencies selected from a range of between 10 kHz to 1 MHz at or near the site of the cancerous tumor located within a bodily tissue. The electric field generating circuit and the control circuitry can be disposed within housing 302. In some embodiments, the electric field generating circuit and the control circuitry are disposed within housing 302.

In some embodiments, the various medical devices herein can deliver one or more electric fields to the cancerous tumor at frequencies selected from a range of from 10 kHz to 1 MHz. In some embodiments, the various medical devices herein can deliver one or more electric fields to the cancerous tumor at frequencies selected from a range of from 300 kHz to 500 kHz. In some embodiments, the various medical devices herein can deliver one or more electric fields to the cancerous tumor at frequencies selected from a range of from 100 kHz to 300 kHz. In some embodiments, the various medical devices herein can deliver one or more electric fields having an electric field strength selected from a range of electric field strengths from 0.25 V/cm to 1000 V/cm. In some embodiments, the various medical devices herein can deliver one or more electric fields having an electric field strength selected from a range of electric field strengths from 1 V/cm to 10 V/cm. In some embodiments, the various medical devices herein can deliver one or more electric fields having an electric field strength selected from a range of electric field strengths from 2 V/cm to 5 V/cm. Additional properties of suitable electric fields for delivery by the various medical devices herein will be discussed in more detail below.

It will be appreciated that the embodiments shown herein include those with leads having wires and electrodes disposed along the longitudinal axis, other medical devices can also include electrodes for generating an electric field at or near the site of a cancerous tumor. In some embodiments, the wires and respective electrodes herein can be disposed on a device substrate. In some embodiments the device substrate can include a rigid body, a stent body, a blunt dissection probe, and the like.

Figure 10:
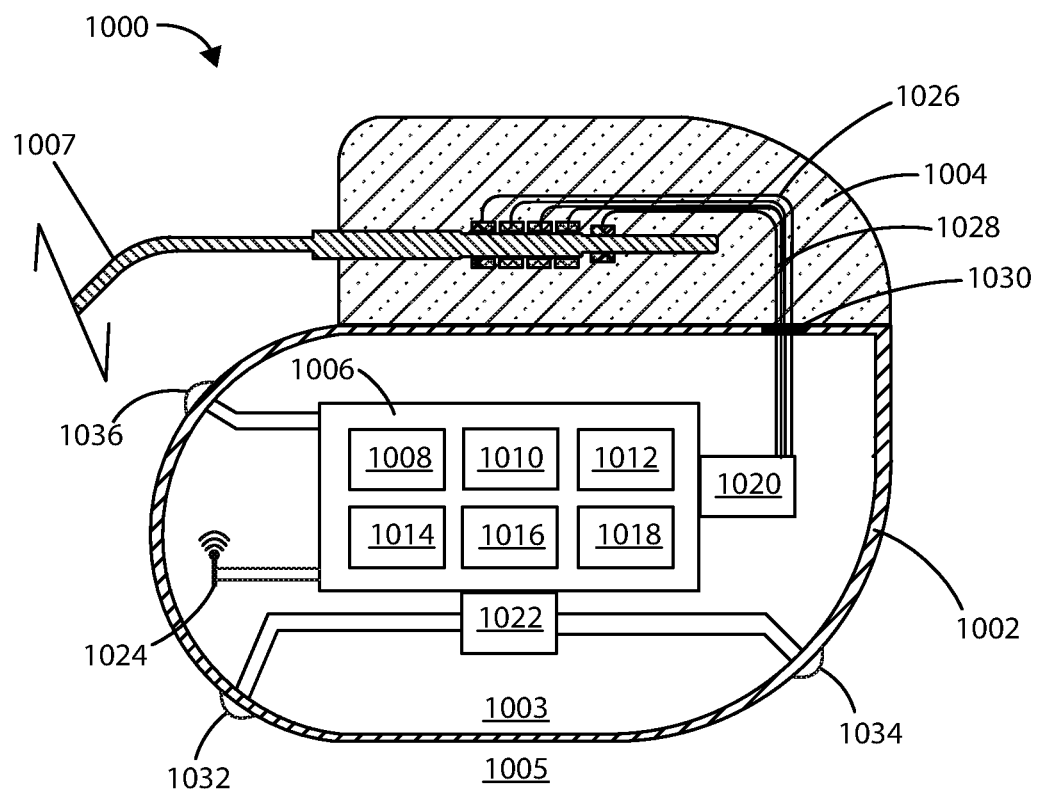
FIG. 10 is a schematic cross-sectional view of a medical device in accordance with various embodiments herein.

Referring now to FIG. 10, a schematic cross-sectional view of exemplary medical device 1000 is shown in accordance with embodiments herein. It will be appreciated the features of medical device 1000 can be included in any of the medical devices described herein. Housing 1002 can define an interior volume 1003 that can be hollow and that in some embodiments is hermetically sealed off from the area 1005 outside of medical device 1000. In other embodiments the housing 1002 can be filled with components and/or structural materials such that it is non-hollow. The medical device 1000 can include control circuitry 1006, which can include various components 1008, 1010, 1012, 1014, 1016, and 1018 disposed within housing 1002. In some embodiments, these components can be integrated and in other embodiments these components can be separate. In yet other embodiments, there can be a combination of both integrated and separate components. The medical device 1000 can also include an antenna 1024, to allow for unidirectional or bidirectional wireless data communication. In some embodiments, the components of medical device 1000 can include an inductive energy receiver coil (not shown) communicatively coupled or attached thereto to facilitate transcutaneous recharging of the medical device via recharging circuitry.

The various components 1008, 1010, 1012, 1014, 1016, and 1018 of control circuitry 1006 can include, but are not limited to, a microprocessor, memory circuit (such as random access memory (RAM) and/or read only memory (ROM)), recorder circuitry, controller circuit, a telemetry circuit, a power supply circuit (such as a battery), a timing circuit, and an application specific integrated circuit (ASIC), a recharging circuit, amongst others. Control circuitry 1006 can be in communication with an electric field generating circuit 1020 that can be configured to generate electric current to create one or more fields. The electric field generating circuit 1020 can be integrated with the control circuitry 1006 or can be a separate component from control circuitry 1006. Control circuitry 1006 can be configured to control delivery of electric current from the electric field generating circuit 1020. In some embodiments, the electric field generating circuit 1020 can be present in a portion of the medical device that is external to the body.

In some embodiments, the control circuitry 1006 can be configured to direct the electric field generating circuit 1020 to deliver an electric field using one or more frequencies selected from a range of within 10 kHz to 1 MHz. In some embodiments, the control circuitry 1006 can be configured to direct the electric field generating circuit 1020 to deliver an electric field at one or more frequencies selected from a range of within 300 kHz to 500 kHz. In some embodiments, the control circuitry 1006 can be configured to direct the electric field generating circuit 1020 to deliver an electric field at one or more frequencies selected from a range of within 100 kHz to 300 kHz. In some embodiments, the control circuitry 1006 can be configured to direct the electric field generating circuit 1020 to periodically deliver an electric field using one or more frequencies greater than 1 MHz.

In some embodiments, the electric field can be effective in disrupting cellular mitosis in cancerous cells. The electric field can be delivered to the site of a cancerous tumor along more than one vector. In some examples, the electric field can be delivered along at least one vector, including at least one of the lead electrodes. In some embodiments, at least two vectors with spatial diversity between the two vectors can be used. The vectors can be spatially separated (e.g., the vectors can be disposed at an angle with respect to one another) by at least about 10, 20, 30, 40, 50, 60, 70, 80 or 90 degrees.

A desired electric field strength can be achieved by delivering an electric current between two electrodes. The specific current and voltage at which the electric field is delivered can vary and can be adjusted to achieve the desired electric field strength at the site of the tissue to be treated. In some embodiments, the control circuitry 1006 can be configured to direct the electric field generating circuit 1020 to deliver an electric field using currents ranging from 1 mAmp to 1000 mAmp to the site of a cancerous tumor. In some embodiments, the control circuitry 1006 can be configured to direct the electric field generating circuit 1020 to deliver an electric field using currents ranging from 20 mAmp to 500 mAmp to the site of a cancerous tumor. In some embodiments, the control circuitry 1006 can be configured to direct the electric field generating circuit 1020 to deliver an electric field using currents ranging from 30 mAmp to 300 mAmp to the site of a cancerous tumor.

In some embodiments, the control circuitry 1006 can be configured to direct the electric field generating circuit 1020 to deliver an electric field using currents including 1 mAmp, 2 mAmp, 3 mAmp, 4 mAmp, 5 mAmp, 6 mAmp, 7 mAmp, 8 mAmp, 9 mAmp, 10 mAmp, 15 mAmp, 20 mAmp, 25 mAmp, 30 mAmp, 35 mAmp, 40 mAmp, 45 mAmp, 50 mAmp, 60 mAmp, 70 mAmp, 80 mAmp, 90 mAmp, 300 mAmp, 125 mAmp, 150 mAmp, 175 mAmp, 400 mAmp, 225 mAmp, 250 mAmp, 275 mAmp, 300 mAmp, 325 mAmp, 350 mAmp, 375 mAmp, 400 mAmp, 425 mAmp, 450 mAmp, 475 mAmp, 500 mAmp, 525 mAmp, 550 mAmp, 575 mAmp, 600 mAmp, 625 mAmp, 650 mAmp, 675 mAmp, 700 mAmp, 725 mAmp, 750 mAmp, 775 mAmp, 800 mAmp, 825 mAmp, 850 mAmp, 875 mAmp, 900 mAmp, 925 mAmp, 950 mAmp, 975 mAmp, or 1000 mAmp. It will be appreciated that the control circuitry can be configured to direct the electric field generating circuit 1020 to deliver an electric field at a current falling within a range, wherein any of the forgoing currents can serve as the lower or upper bound of the range, provided that the lower bound of the range is a value less than the upper bound of the range.

In some embodiments, the control circuitry 1006 can be configured to direct the electric field generating circuit 1020 to deliver an electric field using voltages ranging from 1 $V_{rms}$ to 50 $V_{rms}$ to the site of a cancerous tumor. In some embodiments, the control circuitry 1006 can be configured to direct the electric field generating circuit 1020 to deliver an electric field using voltages ranging from 5 $V_{rms}$ to 30 $V_{rms}$ to the site of a cancerous tumor. In some embodiments, the control circuitry 1006 can be configured to direct the electric field generating circuit 1020 to deliver an electric field using voltages ranging from 10 $V_{rms}$ to 20 $V_{rms}$ to the site of a cancerous tumor.

In some embodiments, the control circuitry 1006 can be configured to direct the electric field generating circuit 1020 to deliver an electric field using one or more voltages including 1 $V_{rms}$, 2 $V_{rms}$, 3 $V_{rms}$, 4 $V_{rms}$, 5 $V_{rms}$, 6 $V_{rms}$, 7 $V_{rms}$, 8 $V_{rms}$, 9 $V_{rms}$, 10 $V_{rms}$, 15 $V_{rms}$, 20 $V_{rms}$, 25 $V_{rms}$, 30 $V_{rms}$, 35 $V_{rms}$, 40 $V_{rms}$, 45 $V_{rms}$, or 50 $V_{rms}$. It will be appreciated that the control circuitry can be configured to direct the electric field generating circuit 1020 to deliver an electric field using a voltage falling within a range, wherein any of the forgoing voltages can serve as the lower or upper bound of the range, provided that the lower bound of the range is a value less than the upper bound of the range.

In some embodiments, the control circuitry 1006 can be configured to direct the electric field generating circuit 1020 to deliver and electric field using one or more frequencies including 10 kHz, 20 kHz, 30 kHz, 40 kHz, 50 kHz, 60 kHz, 70 kHz, 80 kHz, 90 kHz, 300 kHz, 125 kHz, 150 kHz, 175 kHz, 400 kHz, 225 kHz, 250 kHz, 275 kHz, 300 kHz, 325 kHz, 350 kHz, 375 kHz, 400 kHz, 425 kHz, 450 kHz, 475 kHz, 500 kHz, 525 kHz, 550 kHz, 575 kHz, 600 kHz, 625 kHz, 650 kHz, 675 kHz, 700 kHz, 725 kHz, 750 kHz, 775 kHz, 800 kHz, 825 kHz, 850 kHz, 875 kHz, 900 kHz, 925 kHz, 950 kHz, 975 kHz, 1 MHz. It will be appreciated that the electric field generating circuit 1020 can deliver an electric field using a frequency falling within a range, wherein any of the foregoing frequencies can serve as the upper or lower bound of the range, provided that the upper bound is greater than the lower bound.

In some embodiments, the control circuitry 1006 can be configured to direct the electric field generating circuit 1020 to generate one or more applied electric field strengths selected from a range of within 0.25 V/cm to 1000 V/cm. In some embodiments, the control circuitry 1006 can be configured to direct the electric field generating circuit 1020 to generate one or more applied electric field strengths of greater than 3 V/cm. In some embodiments, the control circuitry 1006 can be configured to direct the electric field generating circuit 1020 to generate one or more applied electric field strengths selected from a range of within 1 V/cm to 10 V/cm. In some embodiments, the control circuitry 1006 can be configured to direct the electric field generating circuit 1020 to generate one or more applied electric field strengths selected from a range of within 2 V/cm to 5 V/cm.

In other embodiments, the control circuitry 1006 can be configured to direct the electric field generating circuit 1020 to generate one or more applied electric field strengths including 0.25 V/cm, 0.5 V/cm, 0.75 V/cm, 1.0 V/cm, 2.0 V/cm, 3.0 V/cm, 5.0 V/cm, 6.0 V/cm, 7.0 V/cm, 8.0 V/cm, 9.0 V/cm, 10.0 V/cm, 20.0 V/cm, 30.0 V/cm, 40.0 V/cm, 50.0 V/cm, 60.0 V/cm, 70.0 V/cm, 80.0 V/cm, 90.0 V/cm, 300.0 V/cm, 125.0 V/cm, 150.0 V/cm, 175.0 V/cm, 400.0 V/cm, 225.0 V/cm, 250.0 V/cm, 275.0 V/cm, 300.0 V/cm, 325.0 V/cm, 350.0 V/cm, 375.0 V/cm, 400.0 V/cm, 425.0 V/cm, 450.0 V/cm, 475.0 V/cm, 500.0 V/cm, 600.0 V/cm, 700.0 V/cm, 800.0 V/cm, 900.0 V/cm, 1000.0 V/cm. It will be appreciated that the electric field generating circuit 1020 can generate an electric field having a field strength at a treatment site falling within a range, wherein any of the foregoing field strengths can serve as the upper or lower bound of the range, provided that the upper bound is greater than the lower bound.

In some embodiments, the control circuitry 1006 can be configured to direct the electric field generating circuit 1020 to deliver an electric field via leads 1007 to the site of a cancerous tumor located within a bodily tissue. In other embodiments, the control circuitry 1006 can be configured to direct the electric field generating circuit 1020 to deliver an electric field via the housing 1002 of medical device 1000 to the site of a cancerous tumor located within a bodily tissue. In other embodiments, the control circuitry 1006 can be configured to direct the electric field generating circuit 1020 to deliver an electric field between leads 1007 and the housing 1002 of medical device 1000. In some embodiments, one or more leads 1007 can be in electrical communication with the electric field generating circuit 1020. In some embodiments, the one or more leads 1007 can include one or more electrodes (not shown in FIG. 10) disposed along the length of the leads 1007, where the electrodes can be in electrical communication with the electric field generating circuit 1020.

In some embodiments, various components within medical device 1000 can include an electric field sensing circuit 1022 configured to generate a signal corresponding to sensed electric fields. Electric field sensing circuit 1022 can be integrated with control circuitry 1006 or it can be separate from control circuitry 1006.

Sensing electrodes can be disposed on or adjacent to the housing of the medical device, on one or more leads connected to the housing, on a separate device implanted near or in the tumor, or any combination of these locations. In some embodiments, the electric field sensing circuit 1022 can include a first sensing electrode 1032 and a second sensing electrode 1034. In other embodiments, the housing 1002 itself can serve as a sensing electrode for the electric field sensing circuit 1022. The sensing electrodes 1032 and 1034 can be in communication with the electric field sensing circuit 1022. The electric field sensing circuit 1022 can measure the electrical potential difference (voltage) between the first sensing electrode 1032 and the second sensing electrode 1034. In some embodiments, the electric field sensing circuit 1022 can measure the electrical potential difference (voltage) between the first sensing electrode 1032 or second sensing electrode 1034, and an electrode disposed along the length of one or more leads 1007. In some embodiments, the electric field sensing circuit can be configured to measure sensed electric fields and to record electric field strength in V/cm.

It will be appreciated that the electric field sensing circuit 1022 can additionally measure an electrical potential difference between the first sensing electrode 1032 or the second sensing electrode 1034 and the housing 1002 itself. In other embodiments, the medical device can include a third electrode 1036, which can be an electric field sensing electrode or an electric field generating electrode. In some embodiments, one or more sensing electrodes can be disposed along lead 1007 and can serve as additional locations for sensing an electric field. Many combinations can be imagined for measuring electrical potential difference between electrodes disposed along the length of one or more leads 1007 and the housing 1002 in accordance with the embodiments herein.

In some embodiments, the one or more leads 1007 can be in electrical communication with the electric field generating circuit 1020. The one or more leads 1007 can include one or more electrodes disposed along a longitudinal axis or disposed at the tip of the lead. In some embodiments, various electrical conductors, such as electrical conductors 1026 and 1028, can pass from the header 1004 through a feed-through structure 1030 and into the interior volume 1003 of medical device 1000. As such, the electrical conductors 1026 and 1028 can serve to provide electrical communication between the one or more leads 1007 and control circuitry 1006 disposed within the interior volume 1003 of the housing 1002.

In some embodiments, recorder circuitry can be configured to record the data produced by the electric field sensing circuit 1022 and record time stamps regarding the same. In some embodiments, the control circuitry 1006 can be hard-wired to execute various functions, while in other embodiments the control circuitry 1006 can be directed to implement instructions executing on a microprocessor or other external computation device. A telemetry circuit can also be provided for communicating with external computation devices such as a programmer, a home-based unit, and/or a mobile unit (e.g. a cellular phone, personal computer, smart phone, tablet computer, and the like).

Figure 11:
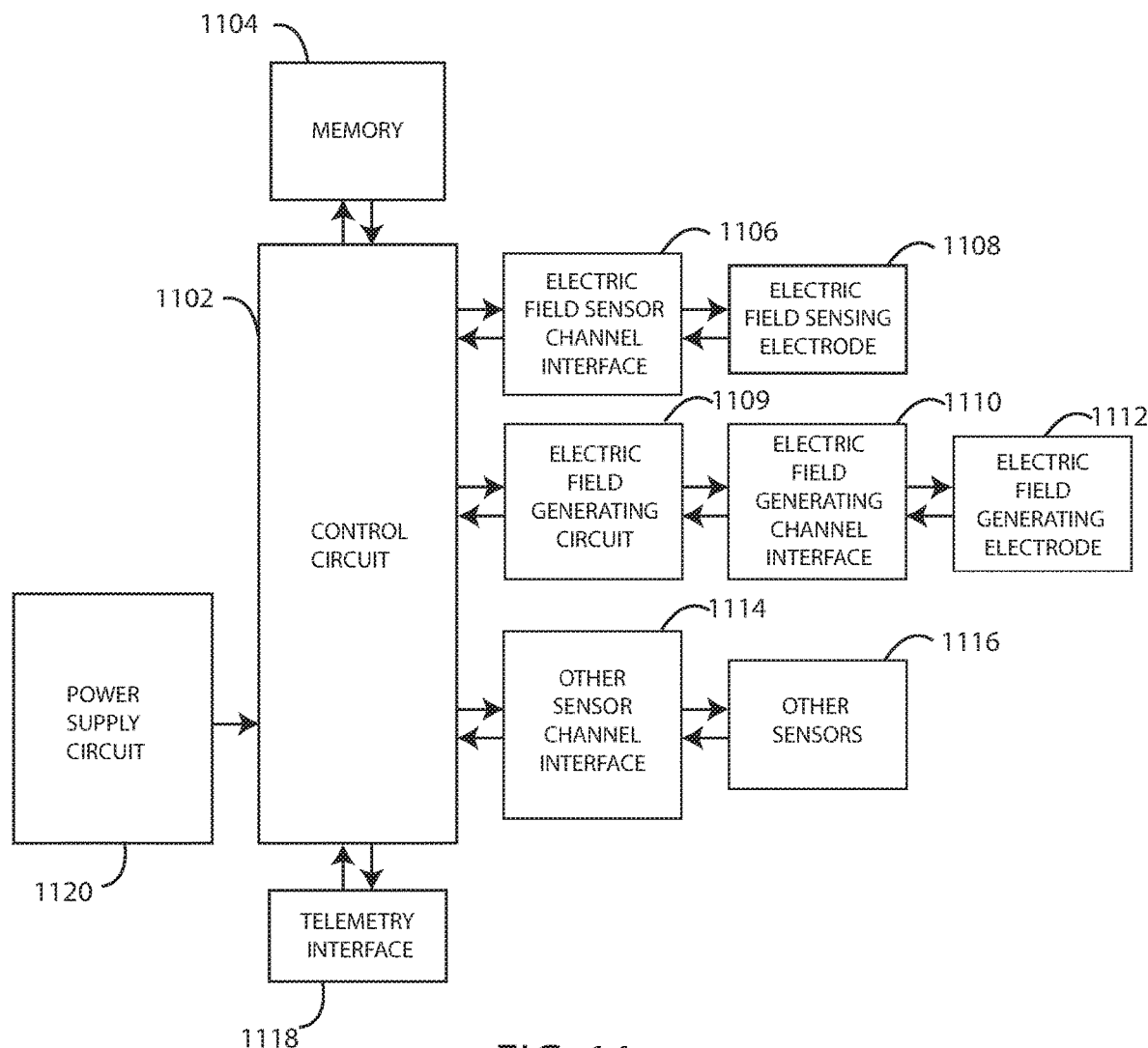
FIG. 11 is a schematic diagram of components of a medical device in accordance with various embodiments herein.

Elements of various embodiments of the medical devices described herein are shown in FIG. 11. However, it will be appreciated that some embodiments can include additional elements beyond those shown in FIG. 11. In addition, some embodiments may lack some elements shown in FIG. 11. The medical devices as embodied herein can gather information through one or more sensing channels and can output information through one or more field generating channels. A microprocessor 1102 can communicate with a memory 1104 via a bidirectional data bus. The microprocessor 1102 can be in electric communication with power supply circuit 1120. The memory 1104 can include read only memory (ROM) or random access memory (RAM) for program storage and RAM for data storage. The microprocessor 1102 can also be connected to a telemetry interface 1118 for communicating with external devices such as a programmer, a home-based unit and/or a mobile unit (e.g. a cellular phone, personal computer, smart phone, tablet computer, and the like) or directly to the cloud or another communication network as facilitated by a cellular or other data communication network. In some embodiments, the medical device can include an inductive energy receiver coil interface (not shown) communicatively coupled or attached thereto to facilitate transcutaneous recharging of the medical device.

The medical device can include one or more electric field sensing electrodes 1108 and one or more electric field sensor channel interfaces 1106 that can communicate with a port of microprocessor 1102. The medical device can also include one or more electric field generating electrodes 1112 and one or more electric field generating channel interfaces 1110 and one or more electric field generating circuits 1109 that can communicate with a port of microprocessor 1102. The medical device can also include one or more other sensors 1116, such as physiological sensors, respiration sensors, or chemical sensors, and one or more other sensor channel interfaces 1114 that can communicate with a port of microprocessor 1102. The sensor channel interfaces 1106, 1110, and 1114 can include various components such as analog-to-digital converters for digitizing signal inputs, sensing amplifiers, registers which can be written to by the control circuitry in order to adjust the gain and threshold values for the sensing amplifiers, source drivers, modulators, demodulators, multiplexers, and the like.

In some embodiments, the physiological sensors can include sensors that monitor temperature, blood flow, blood pressure, and the like. In some embodiments, the respiration sensors can include sensors that monitor respiration rate, respiration peak amplitude, and the like. In some embodiments, the chemical sensors can measure the quantity of an analyte present in a treatment area about the sensor, including but not limited to analytes such as of blood urea nitrogen, creatinine, fibrin, fibrinogen, immunoglobulins, deoxyribonucleic acids, ribonucleic acids, potassium, sodium, chloride, calcium, magnesium, lithium, hydronium, hydrogen phosphate, bicarbonate, and the like. However, many other analytes are also contemplated herein. Exemplary chemical/analyte sensors are disclosed in commonly owned U.S. Pat. No. 7,809,441 to Kane et al., and which is hereby incorporated by reference in its entirety.

Although the other sensors 1116 are shown as part of a medical device in FIG. 11, it is realized that in some embodiments one or more of the other sensors could be physically separate from the medical device. In various embodiments, one or more of the other sensors can be within another implanted medical device communicatively coupled to a medical device via telemetry interface 1118. In yet other embodiments, one or more of the other sensors can be external to the body and coupled to a medical device via telemetry interface 1118. In some embodiments, the other sensors can include drug delivery sensors, biopsy apparatus sensors, optical sensors, or irrigation sensors.

Methods

Figure 12:
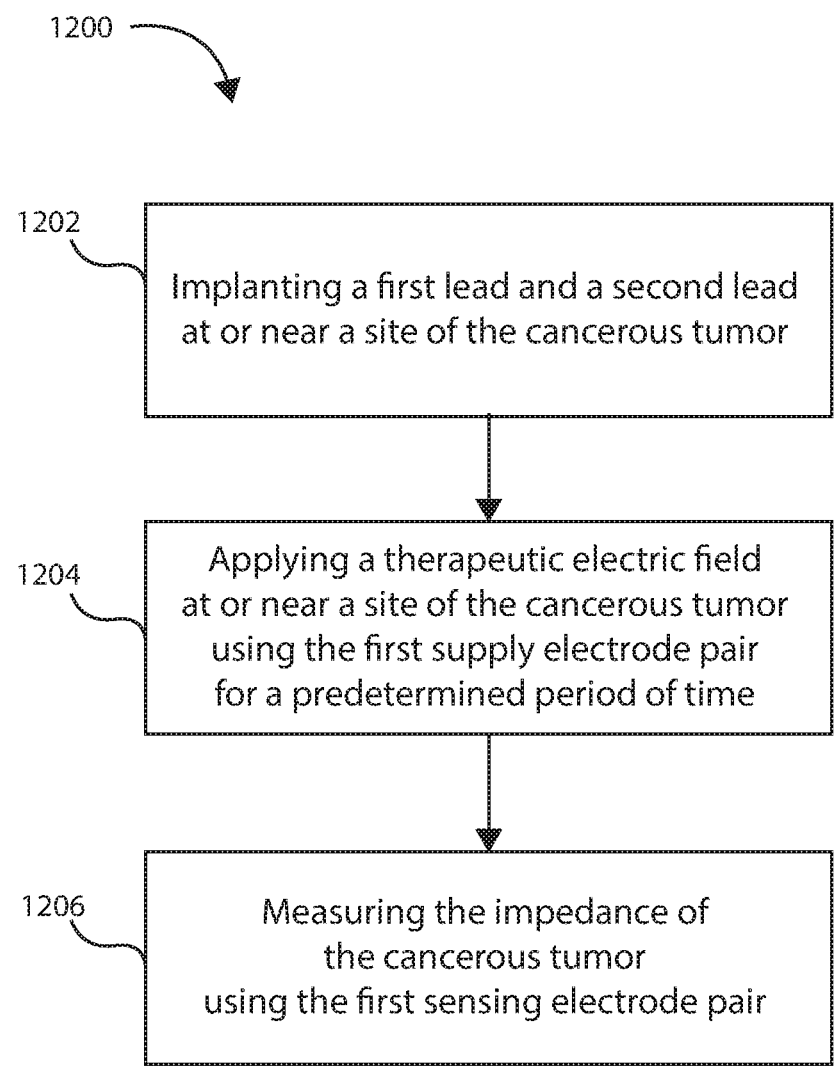
FIG. 12 is a schematic view of a method in accordance with various embodiments herein.

Various methods are can be implemented with the devices described herein. In some embodiments, a method of treating a cancerous tumor can include using four wire impedance measurements to direct therapy. Referring now to FIG. 12, a schematic view of an exemplary method 1200 for treating a cancerous tumor is shown in accordance with the embodiments herein. Method 1200 includes implanting a first lead and a second lead at or near a site of the cancerous tumor at 1202. The first lead can include a first wire and a second wire, and the second lead can include a third wire and a fourth wire. The first wire can be in electrical communication with a first electrode, the second wire can be in electrical communication with a second electrode, the third wire can be in electrical communication with a third electrode, and the fourth wire can be in electrical communication with a fourth electrode. The first electrode and the third electrode can form a first supply electrode pair configured to deliver an electric field at or near a site of the cancerous tumor, and the second electrode and fourth electrode can form a first sensing electrode pair configured to measure impedance of the cancerous tumor independent of an impedance between the sensing electrode pair. The method 1200 can include applying a therapeutic electric field at or near a site of the cancerous tumor using the first supply electrode pair for a predetermined period of time at 1204. The method 1200 can include measuring the impedance of the cancerous tumor using the first sensing electrode pair at 1206. In some embodiments, the first, second, third, and fourth wires and respective first, second, third, and fourth electrodes can be present on one lead or device substrate. In some embodiments the device substrate can include a rigid body, a stent body, a blunt dissection probe, and the like.

In some embodiments, the method 1200 can include measuring a change in the impedance of the cancerous tumor by obtaining multiple measurements over a predetermined amount of time. In some embodiments, the method 1200 can include determining a regression of the cancerous tumor by detecting an increase in the impedance over the predetermined period of time. In some embodiments, the method 1200 can include determining a progression of the cancerous tumor by detecting a decrease in the impedance over the predetermined period of time. Without wishing to be bound by any particular theory, it is believed that a cancerous tumor includes a greater amount of fluid, such as blood, lymph, and/or extracellular fluid within its structure as compared to healthy surrounding tissue. Since aqueous fluids are good conductors of current, an area with greater fluid volume, such as a cancerous tumor, will exhibit an impedance that is less than the impedance within a healthy tissue. In some embodiments, the method 1200 can include adjusting the therapeutic electric field if it is determined that a cancerous tumor is progressing. In some embodiments, adjusting the therapeutic electric field can include increasing the electric field strength, treatment duration, frequency of the electric field, or combining an electric field therapy with a chemotherapeutic agent.

Figure 13:
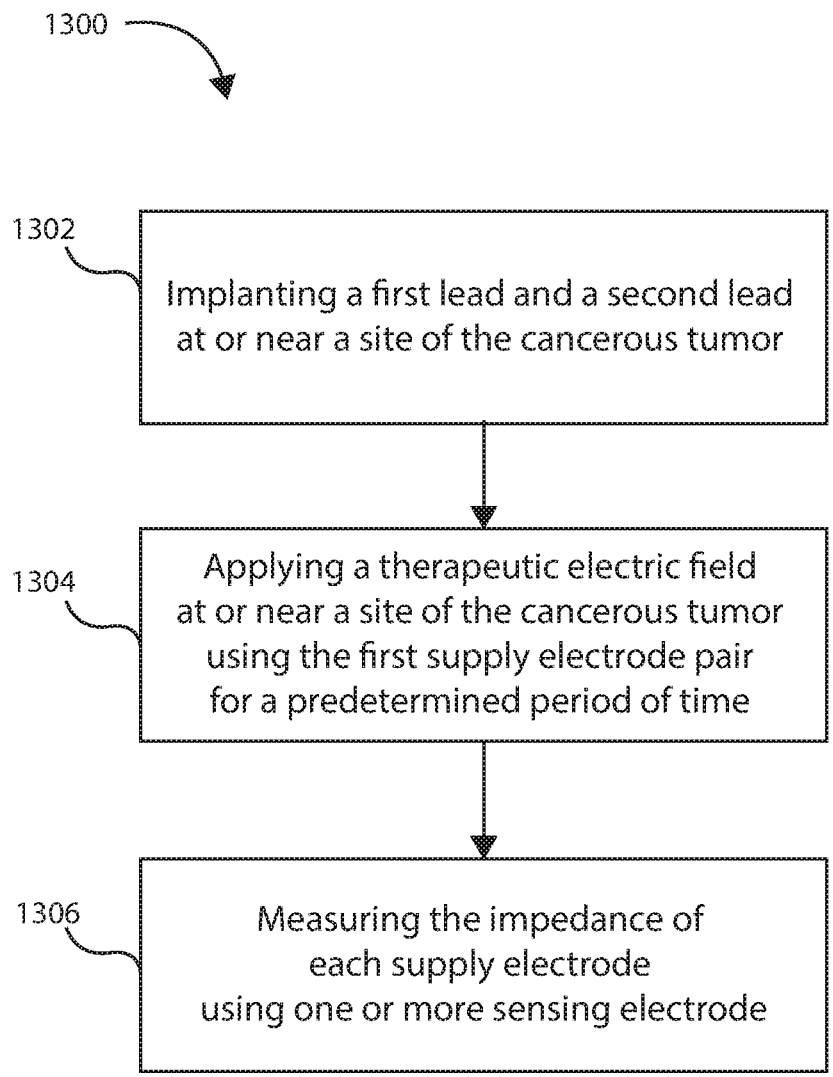
FIG. 13 is a schematic view of a method in accordance with various embodiments herein.

Referring now to FIG. 13, a schematic view of an exemplary method 1300 for treating a cancerous tumor is shown in accordance with the embodiments herein. The method 1300 can include implanting a first lead and a second lead at or near a site of the cancerous tumor at 1302. The first lead and second lead can each include one or more supply electrodes and one or more sensing electrodes. The method 1300 can include applying an electric field at or near the site of the cancerous tumor with the one or more supply electrodes for a predetermined period of time at 1304. The method 1300 can include measuring the impedance of each supply electrode using one or more sensing electrode at 1306. In some embodiments, the method 1300 can include performing unipolar impedance measurements to differentiate the impedance of each supply electrode.

Figure 14:
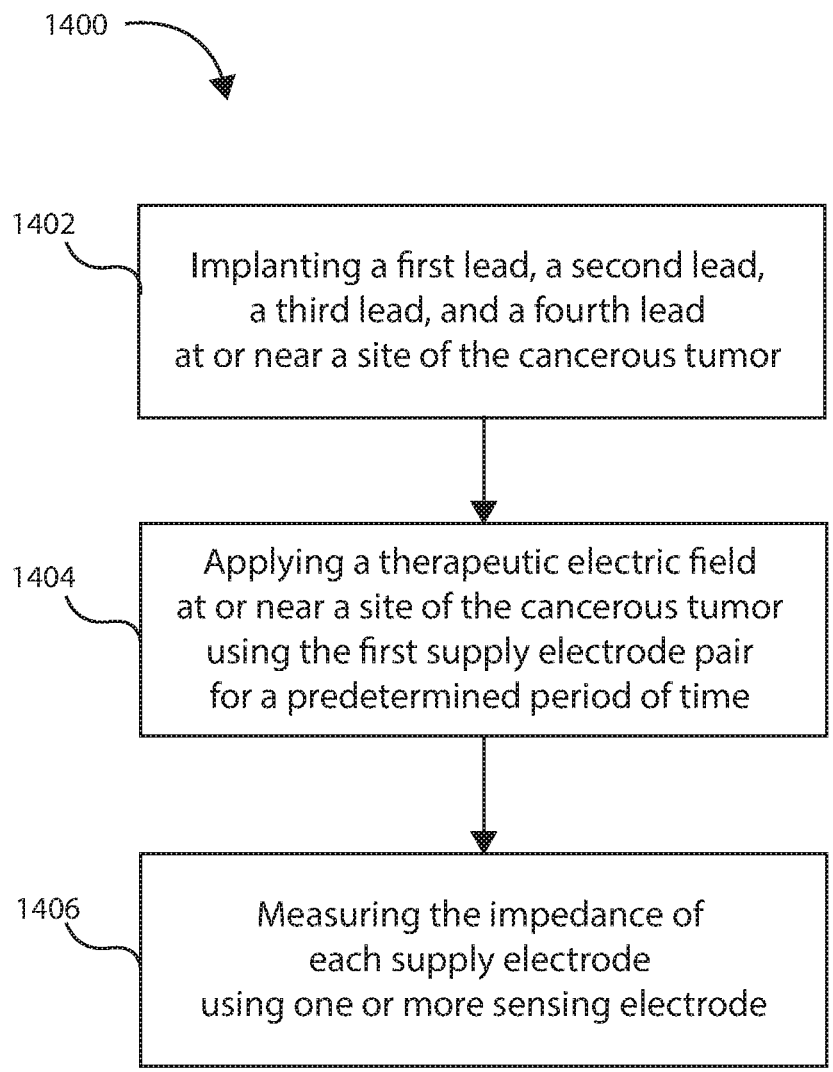
FIG. 14 is a schematic view of a method in accordance with various embodiments herein.

Referring now to FIG. 14, a schematic view of an exemplary method 1400 for treating a cancerous tumor is shown in accordance with the embodiments herein. The method 1400 can include implanting a first lead, a second lead, a third lead, and a fourth lead at or near a site of the cancerous tumor at 1402. The first lead and third lead can each include one or more supply electrodes, and the second lead and fourth lead can each include one or more sensing electrodes. The method 1400 can include applying an electric field at or near the site of the cancerous tumor with the supply electrodes for a predetermined period of time at 1404. The method 1400 can include measuring the impedance of each supply electrode using the one or more sensing electrodes. In some embodiments, the method 1400 can further include measuring the capacitance across the supply electrodes, where the measured capacitance can be used to determine the quality of the supply electrodes at 1406. In embodiments where it is determined that any of the supply electrodes is failing, use of the failing electrode can be discontinued.

Figure 15:
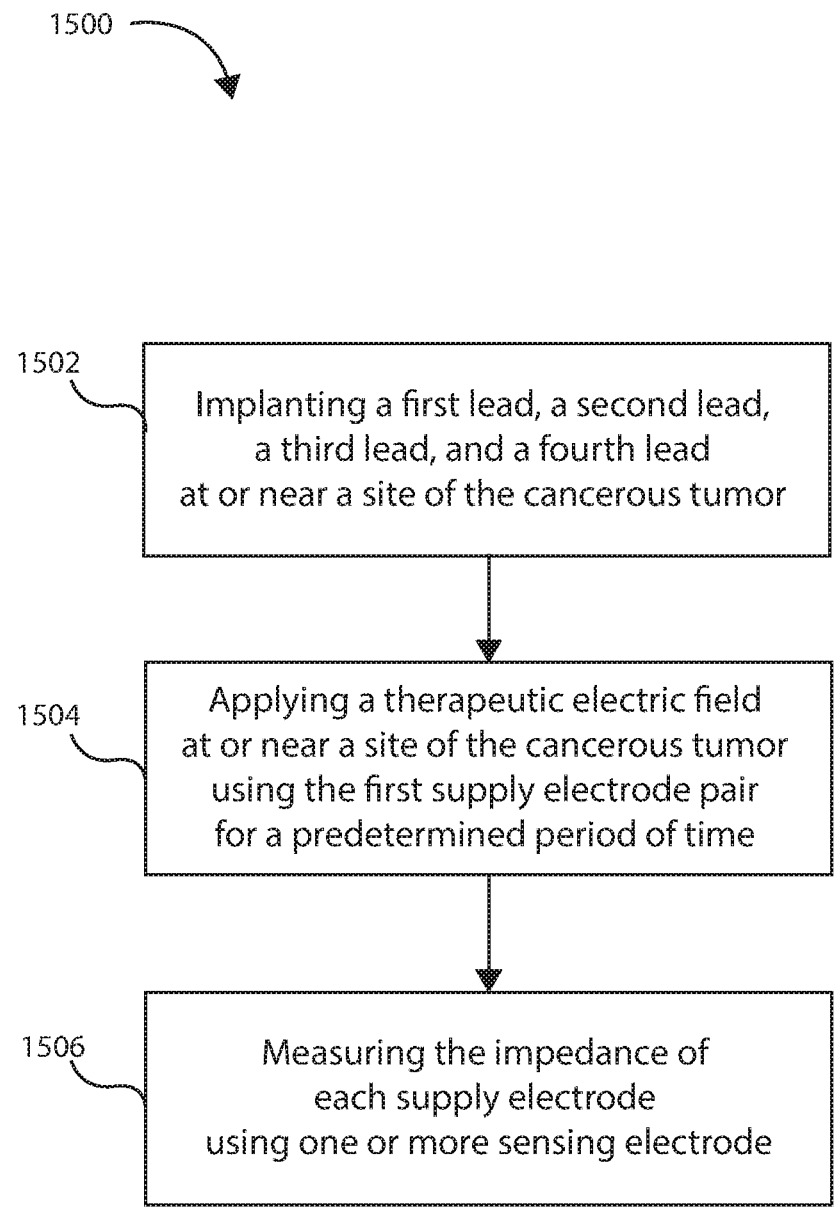
FIG. 15 is a schematic view of a method in accordance with various embodiments herein.

Referring now to FIG. 15, a schematic view of an exemplary method 1500 for treating a cancerous tumor is shown in accordance with the embodiments herein. The method 1500 can include implanting a first lead, a second lead, a third lead, and a fourth lead at or near a site of the cancerous tumor at 1502. The first lead and third lead can each include one or more supply electrodes, and the second lead and fourth lead can each include one or more sensing electrodes. The method 1500 can include applying an electric field at or near the site of the cancerous tumor along a first vector with the one or more supply electrodes for a predetermined period of time at 1504. The method 1500 can include measuring the impedance of each supply electrode along a second vector using the one or more sensing electrodes at 1506. Measuring the impedance of each supply electrode along a second vector can include measuring the impedance of each supply electrode along a second vector that is spatially separate from the first vector along which the one or more electric fields are delivered to the cancerous tumor.

In some embodiments, the method 1500 can include performing unipolar impedance measurements to differentiate the impedance of each supply electrode. In some embodiments, the method 1500 can include implanting any of the first lead, the second lead, the third lead, or the fourth lead at or near the site of the cancerous tumor through a natural body orifice or duct. The natural body orifice can be selected from any of the nasal passages, the ear canal, the mouth, the esophagus, the trachea, the urethra, the vagina, the small intestine, the anus, or the colon. The duct can be selected from any of the common bile duct, the bile duct, the pancreatic duct, the common hepatic duct, the ureters, the Eustachian tubes, or the fallopian tubes.

In the various methods described herein, applying the one or more electric fields can include at least applying an electric field at various electric field strengths. By way of example, the one or more electric fields can be applied to the cancerous tumor at electric field strengths selected from a range of electric field strengths from 0.25 V/cm to 1000 V/cm. In some embodiments, the one or more electric fields can be applied to the cancerous tumor at electric field strengths selected from a range of electric field strengths from 1 V/cm to 10 V/cm. In some embodiments, the one or more electric fields can be applied to the cancerous tumor at electric field strengths selected from a range of electric field strengths from 2 V/cm to 5 V/cm. In some embodiments, the field strength can be greater than or equal to 0.25 V/cm, 0.50 V/cm, 0.75 V/cm, 1.00 V/cm, 1.25 V/cm, 1.50 V/cm, 1.75 V/cm, 2.00 V/cm, 2.25 V/cm, 2.50 V/cm, 2.75 V/cm, 3.00 V/cm, 3.25 V/cm, 3.50 V/cm, 3.75 V/cm, 4.00 V/cm, 4.25 V/cm, 4.50 V/cm, 4.75 V/cm, 5.00 V/cm, 5.25 V/cm, 5.50 V/cm, 5.75 V/cm, 6.00 V/cm, 6.25 V/cm, 6.50 V/cm, 6.75 V/cm, 7.00 V/cm, 7.25 V/cm, 7.50 V/cm, 7.75 V/cm, 8.00 V/cm, 8.25 V/cm, 8.50 V/cm, 8.75 V/cm, 9.00 V/cm, 9.25 V/cm, 9.50 V/cm, 9.75 V/cm, 10 V/cm, 20 V/cm, 30 V/cm, 40 V/cm, 50 V/cm, 60 V/cm, 70 V/cm, 80 V/cm, 90 V/cm, 300 V/cm, 150 V/cm, 400 V/cm, 250 V/cm, 300 V/cm, 350 V/cm, 400 V/cm, 450 V/cm, 500 V/cm, 550 V/cm, 600 V/cm, 650 V/cm, 700 V/cm, 750 V/cm, 800 V/cm, 850 V/cm, 900 V/cm, 950 V/cm, or 1000 V/cm, or can be an amount falling in a range within any of the foregoing.

In the various methods described herein, applying the one or more electric fields can include at least applying an electric field at various frequencies. The one or more electric fields can be applied to the cancerous tumor at frequencies selected from a range within 10 kilohertz (kHz) to 1 megahertz (MHz). In some embodiments, the one or more electric fields can be applied to the cancerous tumor at frequencies selected from a range within 300 kHz to 500 kHz. In some embodiments, the one or more electric fields can be applied to the cancerous tumor at frequencies selected from a range within 100 kHz to 300 kHz. In some embodiments, the frequency of the one or more applied electric fields can be greater than or equal to 10 kHz, 20 kHz, 30 kHz, 40 kHz, 50 kHz, 60 kHz, 70 kHz, 80 kHz, 90 kHz, 300 kHz, 125 kHz, 150 kHz, 175 kHz, 400 kHz, 225 kHz, 250 kHz, 275 kHz, 300 kHz, 325 kHz, 350 kHz, 375 kHz, 400 kHz, 425 kHz, 450 kHz, 475 kHz, 500 kHz, 525 kHz, 550 kHz, 575 kHz, 600 kHz, 625 kHz, 650 kHz, 675 kHz, 700 kHz, 725 kHz, 750 kHz, 775 kHz, 800 kHz, 825 kHz, 850 kHz, 875 kHz, 900 kHz, 925 kHz, 950 kHz, 975 kHz, or 1 MHz or can be an amount falling in a range within any of the foregoing.

In the various methods described herein, applying the one or more electric fields can include at least applying an electric field for various predetermined time periods. The one or more electric fields can be applied at or near the site of the cancerous tumor over a predetermined time period selected from a range of predetermined time periods from 1 minute to 24 hours. In some embodiments, the one or more electric fields can be applied at or near the site of the cancerous tumor over a predetermined time period can be greater than or equal to 1, 10, 20, 30, 40, or 50 minutes, or 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, or 48 hours, or can be an amount falling in a range within any of the foregoing.

In the various methods described herein, administering a chemotherapeutic agent can include administering the chemotherapeutic agent for various predetermined time periods. The chemotherapeutic agent can be administered at or near the site of the cancerous tumor over a predetermined time period selected from a range of predetermined time periods from less than 1 minute to 600 minutes. In some embodiments, the chemotherapeutic agent can be administered at or near the site of the cancerous tumor over a predetermined time period can be greater than or equal to 1 sec., 5 sec., 10 sec., 15 sec., 20 sec., 25 sec., 30 sec., 35 sec., 40 sec., 45 sec., 50 sec., 55 sec., or 60 sec., 5 min., 10 min., 15 min., 20 min., 25 min., 30 min., 35 min., 40 min., 45 min., 50 min., 55 min., 60 min, 120 min, 180 min, 240 min, 300 min, 360 min, 420 min, 480 min, 540 min, or 600 min, or can be an amount falling in a range within any of the foregoing.

In the various methods described herein, applying the one or more electric fields at or near the site of the cancerous tumor can include applying the one or more electric fields to the exterior or interior of the subject. In some embodiments, applying the one or more electric fields to the cancerous tumor can include applying the one or more electric fields entirely to the exterior of the subject at or near the site of the cancerous tumor. In some embodiments, applying the one or more electric fields to the cancerous tumor can include applying the one or more electric fields entirely to the interior of the subject at or near the site of the cancerous tumor. In some embodiments, applying the one or more electric fields to the cancerous tumor can include applying the one or more electric fields at least partially to the exterior of the subject at or near the site of the cancerous tumor. In some embodiments, applying the one or more electric fields to the cancerous tumor can include applying the one or more electric fields at least partially to the interior of the subject at or near the site of the cancerous tumor. In other embodiments, applying the one or more electric fields to the cancerous tumor can include applying the one or more electric fields partially to the interior and partially to the exterior of the subject at or near the site of the cancerous tumor.

Impedance Measurements

Feedback obtained during electric field therapy can be used to monitor the effectiveness of treating a cancerous tumor with the therapy. Data can be measured for parameters such as impedance, capacitance, field strength, etc. to direct a particular course of treatment. Without being bound by any particular theory, it is believed that a cancerous tumor has a particular impedance associated therewith. The impedance associated with a tumor can change as the size or cellular makeup of the tumor changes. Therefore, impedance can be monitored during the course of an electric field therapy in order to determine if the cancerous tumor is responding to therapy. In some instances, an increase in impedance of the tissue in a treatment area including a cancerous tumor can be indicative of tumor regression. In other instances, a decrease or no observed change in impedance of the tissue in a treatment area can be indicative of tumor progression or lack of change in the tumor respectively. Other physiological properties associated with a cancerous tumor, such as blood flow, metabolite concentrations, systemic cancer markers, and temperature can also be used in conjunction with impedance analysis to monitor the progression or regression of a cancerous tumor in response to electric field therapy.

Ohm's law provides that electrical potential, current and impedance are interrelated (V=IR or V=IZ). Thus, by knowing one variable (e.g., such as a supplied current) and measuring another (e.g., such as measuring voltage drop), the third variable can be calculated. In some embodiments herein, impedance (Z) can be measured by taking the voltage and dividing by the current. Within the body, impedance can be influenced by a number of factors, including but not limited to components in contact with an electric field such as cell type, including muscle, fat, connective tissue, and bone; cell density, cell size; electrolyte concentrations, etc. In some embodiments, electric field sensing or electric field generating electrodes can serve as impedance monitoring electrodes. It will be appreciated that different tissues will have different impedances at a given frequency. As such, in some embodiments, measuring impedance at one or more frequencies at any given location is contemplated. In some embodiments, impedance can be measured at frequencies within the range of treatment frequencies. In some embodiments, impedance can be measured at frequencies outside of treatment frequencies. In some embodiments, impedance can be measured at both frequencies within the range of treatment frequencies and frequencies outside of treatment frequencies.

In some embodiments, as impedance changes within a cancerous tumor, administering an electric field to the cancerous tumor can change based on the measured impedance. Without being bound by any particular theory, it is believed that the impedance within a cancerous tumor is relatively low when compared to non-cancerous or necrotic tissue. This phenomenon allows impedance to be monitored as a function of therapy duration and to serve as a diagnostic tool in assessing whether or not a tumor is responding to an electric field therapy. If the impedance within a treatment area increases (across a fixed distance or area as a result of the low-impedance tumor tissue shrinking and non-cancerous tissue occupying the remaining space) then this can be taken as an indication that the electric field therapy is effectively decreasing the size of the cancerous tumor. However, if the impedance within a treatment area decreases or stays the same across a fixed distance or area then this can be taken as an indication that the electric field therapy is not decreasing the size of the cancerous tumor. As such, electric field therapies can be tailored to a particular cancerous tumor in order to effectively decrease the size of the cancerous tumor. By way of example, one or more of the amplitude, frequency, pulse width, waveform, directionality, and/or duty cycle of the electric field therapy can be modulated and/or changed.

In some embodiments, low-frequency impedance through a particular cancerous tumor can be used to measure conductivity through the tumor and can be used as an indicator of tissue progression or regression. In some embodiments, high-frequency impedance through a particular cancerous tumor can be used to measure permittivity and capacitive properties of the tumor and can also be used as an indicator of tissue progression or regression. In some embodiments, low-frequency impedance can be measured at frequencies of about 1 Hz to about 10 Hz. In some embodiments, high-frequency impedance can be measured at frequencies of about 10 Hz to about 1 Mz. In some embodiments, high-frequency impedance can be measured at frequencies of about 300 kHz to about 300 kHz. In various embodiments, a medical device including one or more components described with respect to FIGS. 3 to 10 can be configured to execute one or more operations described with respect to the methods embodied in FIGS. 12 to 15.

Applied Electric Fields

The electric fields applied to the cancerous tumors using the methods herein can be applied using a variety of modalities. Exemplary therapeutic parameter sets can include those that implement the following concepts: sweeping through a range of frequencies; stacking of one or more frequencies simultaneously; stepping through one or more frequencies sequentially; the spatial or temporal delivery of one or more electric fields; sweeping through a range of electric field strengths; applying an effective rotating electric field; modulating a voltage control mode or a current control mode; implementing one or more duty cycles; pulse width modulation; manipulation of the electrical waveform shape and/or pulse sequence; and the occasional use of high frequency or high electric fields strength pulses.

The therapeutic parameter sets can be programmed into a medical device to operate autonomously, or they can be queried and manipulated by the subject or a clinician using an external computation device such as a programmer, a home-based unit, and/or a mobile unit (e.g. a cellular phone, personal computer, smart phone, tablet computer, and the like). In other embodiments, the therapeutic parameter sets can be wirelessly communicated to the medical device from an external computation device. Frequencies and/or electric field strengths suitable for use in any of the therapeutic parameter sets herein are discussed above with respect to electric field generating circuit. In some embodiments, one or more therapeutic parameter sets can be implemented simultaneously. In other embodiments, one or more therapeutic parameter sets can be implemented in an alternating fashion. In some embodiments, the one or more electric fields can be effective to prevent and/or disrupt cellular mitosis in a cancerous cell.

Figure 16:
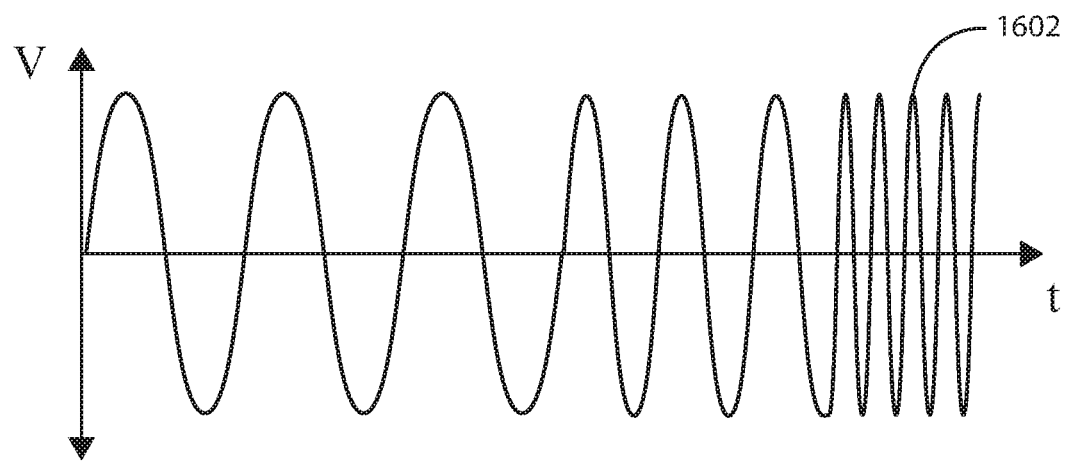
FIG. 16 is a plot of an exemplary electric field in accordance with various embodiments herein.
Figure 17:
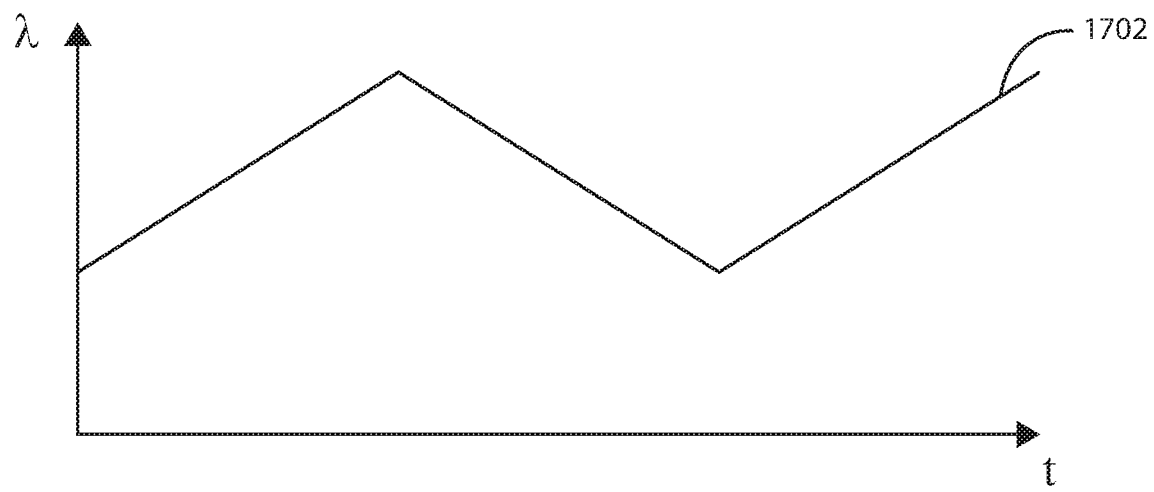
FIG. 17 is a plot of an exemplary electric field in accordance with various embodiments herein.

By way of example, an electric field can be applied to the site of a cancerous tumor by sweeping through a range of frequencies. Referring now to FIG. 16, exemplary plot 1602 shows an alternating electric field, where the frequency of the increases over time. Similarly, FIG. 17 shows the change in frequency as a function of time in exemplary plot 1702 during a programmed therapy parameter. In some embodiments, a frequency sweep can include sweeping from a minimum frequency up to a maximum frequency. In some embodiments, a frequency sweep can include sweeping from a maximum frequency down to a minimum frequency. In other embodiments, sweeping from a minimum frequency up to a maximum frequency and sweeping from the maximum frequency down to the minimum frequency can be repeated as many times as desired throughout the duration of the delivery of the electric field from the electric field generating circuit.

As therapy progresses during a frequency sweep, it may be desired to alternate between frequency ranges so that as the cells within a population change in size and number in response to therapy, more cells can be targeted. For example, in some embodiments, a frequency sweep can include alternating between a first frequency sweep covering a range of about 100 kHz to 300 kHz and a second frequency sweep covering a range about 200 kHz to 500 kHz. It will be appreciated that sweeping through a first and second frequency range as described can be performed indefinitely throughout the course of the therapy. In some embodiments, the second frequency sweep (range) can be at higher frequencies than the first frequency sweep (range). In some embodiments, the first frequency sweep (range) can be at higher frequencies than the second frequency sweep (range).

Frequency ranges for the first and second frequency ranges can be any range including specific frequencies recited above with respect to electric field generating circuit, provided that the lower end of each range is a value less than the upper end of each range. At times, it may be beneficial to have some amount of overlap between the frequency range of the first and second frequency sweep.

Leads and Electrodes

The leads described herein can be placed into the body at or near the site of a cancerous tumor using a number of techniques. Placement of one or more leads can include using techniques such as transvascular placement, tunneling into the subcutaneous space, and/or surgical placement. In some embodiments, the placement of one or more leads can include placement via one or more natural body orifices. The medical devices herein can be configured for implanting any of the first lead, the second lead, the third lead, the fourth lead, etc., at or near the site of the cancerous tumor through a natural body orifice or duct. In some embodiments, the natural body orifice can include any of the nasal passages, the ear canal, the mouth, the esophagus, the trachea, the urethra, the vagina, the small intestine, the anus, or the colon. In some embodiment, a suitable duct can include those accessible via the gastrointestinal or genitourinary systems, including the common bile duct, the bile duct, the pancreatic duct, the common hepatic duct, the ureters, the Eustachian tubes, or the fallopian tubes. The leads can be placed adjacent to or within a cancerous tumor. In some embodiments, multiple leads can be used near to or far from the cancerous tumor.

In the medical devices described herein, it will be appreciated that one or more unipolar or multipolar leads can be used in accordance with the embodiments herein. In some embodiments, a combination of unipolar and multipolar leads can be used. In other embodiments, a circular lead, clamp lead, cuff lead, paddle lead, or patch lead can be used.

In some embodiments one or more leads described herein can be placed in the subcutaneous space. Electrodes on leads placed in the subcutaneous space can be used as the primary near-field generating electrode or as a far-field field generating electrode. In some embodiments, electrodes on leads placed in the subcutaneous space can be used as the primary near-field generating electrode or as a far-field field generating electrode in conjunction with the housing of a medical device. Likewise, one or more leads can be placed transvascularly to act as far-field field generating electrodes in conjunction with an electrode at or near the site of the cancerous tumor or in conjunction with the housing of a medical device.

The leads and electrodes described herein can include additional functional and structural features. In some embodiments, the leads can include those that are compatible with imaging and treatment techniques, including but not limited to MRI (magnetic resonance imaging), X-ray imaging, deep brain stimulation techniques, and/or radiation therapy. In some embodiments, the leads can include one or more conductor cores made from conducting materials. The conductor cores can be formed from conducting materials including metals and/or other conducting materials. Metals can include, but are not limited to, palladium, platinum, silver, gold, copper, aluminum, various alloys including stainless steel, nickel-cobalt alloys such as MP35N® and the like. In some embodiments, the conductor core can be a multifilar coil, including but not limited to a bifilar coil, a trifilar coil, and a quadfilar coil.

In some embodiments, electrodes can be disposed along the length of one or more leads as described herein. Suitable materials for use in the electrodes described herein can include metals such as palladium, to minimize coupling and artifact generation in magnetic fields. In some embodiments, electrodes can be made from other metals and/or other conducting materials. Metals can include, but are not limited to, palladium, platinum, platinum alloys such as platinum-iridium alloy, gold, copper, tantalum, titanium, various alloys including stainless steel, and the like. In some embodiments, electrodes can be in the form of wound coils that can provide an added benefit of increased surface area without compromising flexibility of the electrodes. In some embodiments, the implantable device housing can serve as an electrode.

The leads described herein can also include one or more electrodes disposed along the length of the lead. The leads can include two or more electrodes disposed along the length of the lead. In some embodiments, the electrodes can be tip electrodes found at the distal end of the lead. In other embodiments, the electrodes can be ring electrodes found along the lead but not at the tip of the lead.

In some embodiments, the electrodes can be coil electrodes. In some embodiments, a ring or tip electrode can be positioned in or adjacent to a tumor or cancerous tissue and a coil electrode can be positioned farther from the tumor or cancerous tissue in order to help provide spatial diversity to the generated electric fields. In some embodiments, one or more electrodes can have a length along the lengthwise axis (e.g., proximal to distal axis) of about 0.5, 1, 1.5, 2, 3, 4, 5, 7.5, 10, 15, 20, 30, 40, 50, 75, 100 mm or more. In some embodiments, one or more of the electrodes can have a length falling within a range wherein any of the foregoing distances can serve as the upper or lower bound of the range, provided that the upper bound is greater than the lower bound.

The leads can be unipolar, bipolar, or multipolar. In some embodiments, a unipolar lead can include a lead that generates an electric field between one electrode and the housing of the medical device. In some embodiments, a bipolar lead can include a lead that can generate and electric field between two electrodes disposed along the lead, or between both electrodes and the housing of the medical device. In some embodiments, a multipolar lead can include a lead that can generate an electric field between the more than two electrodes disposed along the lead, between more than two electrodes and the housing of the medical device, or any number of combinations of configurations of electrodes and the housing of the medical device.

The leads herein can include one or more optical emitters along the length of the lead. Optical emitters suitable for use herein can include those that emit light that falls anywhere along the visible spectrum from about 350 nm to 950 nm. Suitable optical emitters can include light emitting diodes or laser diodes. Suitable LEDs can be made from one or more of gallium arsenide (GaAs), gallium phosphide (GaP), gallium arsenide phosphide (GaAsP), silicon carbide (SiC) or fallium indium nitride (GaInN). In some embodiments, the LEDs suitable for use herein can include an LED capable of emitting only one color, or a mono-color LED; an LED capable of emitting two colors, or a bi-color LED; an LED capable of emitting three colors, or a tri-color LED; or an LED capable of emitting more than three colors. The LEDs can be in electrical communication with control circuitry within the housing of the medical devices described herein. In some embodiments, one or more laser diodes can be included along the leads herein, and the laser diodes can be in optical communication with one or more optical fibers disposed within the leads and used for transmitting light from a laser source to a laser diode.

The electrodes suitable for use here can be made of conductive polymers such as carbon filled silicone, polyacetylene, polypyrrole, polyaniline, polythiophene, polyfuran, polyisoprene, polybutadiene, polyparaphenylene, and the like. In other embodiments, the electrodes can be insulated. In some embodiments, the insulation surrounding and electrode can include microporous insulators to prevent cellular apposition, yet still allow for current flow. Microporous insulators can be made from a number of the insulating materials described herein, including but not limited to polytetrafluoroethylene (ePTFE), polyethylene-co-tetrafluoroethene (ETFE), polyurethanes, silicones, poly(p-xylylene) polymers such as Parylene polymers, polyether block amides such as PEBAX®, nylons, or derivatives thereof. In some embodiments, the electrodes can be coated with various materials, including but not limited to hydrogels or fractal coatings such as iridium oxide, titanium oxide, tantalum pentoxide, other metal oxides, poly(p-xylylene) polymers such as Parylene, and the like.

A number of lead fixation techniques and configurations can be used in accordance with the embodiments herein. Some non-limiting examples of lead fixation techniques can include biocompatible glue fixation, talon fixation, helix coil fixation, passive centering of the lead in the vascular system, tine fixation within the localized vascular system, spiral bias fixation within the localized vascular system, compression fixation, suture sleeve fixation, and the like. In some examples, the leads embodied herein can be placed within the vascular system surrounding or adjacent to the site of the cancerous tumor. In other embodiments, the leads embodied herein can be place surgically at or within or surrounding the site of the cancerous tumor.

The leads suitable for use herein can also include one or more open lumens that run the entire longitudinal length of, or a select portion of the longitudinal length of the lead. In some embodiments, the open lumen can include an integrated biopsy apparatus suitable for obtaining biopsy samples from a cancerous tumor site on a periodic basis to monitor disease progression and/or regression. Leads having an open lumen can also be configured to include an integrated drug delivery lumen that can deliver one or more drugs, such as steroids or chemotherapy agents, to the site of the tumor in a single bolus or periodically via a metered pump. The leads can include one or more portals disposed along the length of the lead to provide an outlet for drug delivery at or near the site of a cancerous tumor.

In some embodiments a portion of the lead or the entire lead can include a drug eluting coating. In some embodiments, the drug eluting coating can include an anti-inflammatory agent, such as a steroid. In some embodiments, the steroid can be dexamethasone. In other embodiments, the drug eluting coating can include a chemotherapy agent. In some embodiments, the chemotherapy agent can include a taxane or derivatives thereof, including but not limited to paclitaxel, docetaxel, and the like. In other embodiments, the drug eluting coating can be configured to release additional classes of chemotherapy agents, including, but not limited to alkylating agents, plant alkaloids such as vinca alkaloids, cytotoxic antibiotics, topoisomerase inhibitors, and the like. In some embodiments, the drug eluting coating can be configured to release the drug from the coating in a time-release fashion.

The leads herein can adopt a number of shapes or configurations. In some embodiments, the leads can be linear and in other embodiments the leads can be circular. A circular lead may be a completely closed loop or it may be a semi-closed loop. In some embodiments, the lead can include a bendable core that can allow the lead to be shaped into many configurations, including but not limited to a U shape, an S shape, a spiral shape, a half circle, an oval, and the like.

In yet other examples, the leads suitable for use herein can include fluorimetric or magnetic markers that can assist the clinician in precise placement at or near the site of a cancerous tumor. The leads can also include integrated pH sensors for detecting the change in the pH at or near the cancerous tumor or other chemical sensors suitable for analyzing the concentration of a chemical analyte of interest.

Electric Field Generators

The medical devices embodied herein can include electric field generators particularly suited for therapeutic and diagnostic techniques used during the course of treatment for a cancerous tumor. In some embodiments, the electric field generators suitable for use herein can include those that have been treated by radiation hardening to make the components resistant to the damaging effects of radiation therapy treatments often prescribed as a main line treatment for cancerous tumors. Electric field generators can include components such as those described in reference to FIGS. 3 and 5 above.

Electric field generators embodied herein can be programmed with any number of therapeutic parameter sets as described. The electric field generators can be programmed prior to implant, or they can be programmed by a clinician using an external computation device such as a programmer, a home-based unit, and/or a mobile unit (e.g. a cellular phone, personal computer, smart phone, tablet computer, and the like). In some embodiments, therapy parameters can be delivered to the electric field generator via a telemetry circuit. In some embodiments, the electric field generator can include a recharge circuit communicatively coupled to a receiver coil to facilitate transcutaneous recharging of the medical device. In some embodiments, the electric field generator can communicate wirelessly between the receiver coil and an external charging device.

Further Embodiments

In an embodiment, a medical device for treating a cancerous tumor is included having a first lead can include a first wire and a second wire; a second lead can include a third wire and a fourth wire; a first electrode in electrical communication with the first wire, a second electrode in electrical communication with the second wire, a third electrode in electrical communication with the third wire, and a fourth electrode in electrical communication with the fourth wire; wherein the first electrode and the third electrode form a supply electrode pair configured to deliver one or more electric fields at or near a site of the cancerous tumor; and wherein the second electrode and the fourth electrode form a sensing electrode pair configured to measure an impedance of the cancerous tumor independent of an impedance of the first electrode, the first wire, the third electrode, the third wire, and components in electrical communication therewith.

In an embodiment, the medical device can include an electric field generating circuit configured to generate the one or more electric fields.

In an embodiment, the first lead and the second lead are each in electrical communication with the electric field generating circuit.

In an embodiment, the medical device can further include a control circuitry in communication with the electric field generating circuit, the control circuitry configured to control delivery of the one or more electric fields from the electric field generating circuit.

In an embodiment, the control circuitry causes the electric field generating circuit to generate one or more electric fields at frequencies selected from a range of between 10 kHz to 1 MHz at or near the site of the cancerous tumor located within a bodily tissue.

In an embodiment, the medical device is configured to be implanted entirely within a subject.

In an embodiment, the medical device is configured to be partially implanted within a subject.

In an embodiment, the one or more electric fields are delivered to the cancerous tumor at frequencies selected from a range of from 100 kHz to 300 kHz.

In an embodiment, the first lead and the second lead are each in electrical communication with the electric field generating circuit.

In an embodiment, the first wire, the second wire, the third wire, and the fourth wire are electrically insulated from one another.

In an embodiment, a current flow through the second electrode, the second wire, the fourth electrode, the fourth wire, and components in electrical communication therewith is negligible.

In an embodiment, a current flow through the second electrode, the second wire, the fourth electrode, the fourth wire, and components in electrical communication therewith is less than 100 pA.

In an embodiment, the first electrode and the second electrode of the first lead are spatially separated along a longitudinal axis of the first lead by at least 1 mm; and wherein the third electrode and the fourth electrode of the second lead are spatially separated along a longitudinal axis of the second lead by at least 1 mm.

In an embodiment, the one or more electric fields are effective to prevent and/or disrupt cellular mitosis in a cancerous cell.

In an embodiment, the medical device is configured to be implanted entirely within a subject.

In an embodiment, the medical device is configured to be partially implanted within a subject.

In an embodiment, the medical device is configured to be entirely external to a subject.

In an embodiment, the one or more electric fields are delivered to the cancerous tumor at frequencies selected from a range of from 10 kHz to 1 MHz.

In an embodiment, the one or more electric fields are applied to the cancerous tumor at frequencies selected from a range of from 100 kHz to 500 kHz.

In an embodiment, the one or more electric fields are delivered to the cancerous tumor at frequencies selected from a range of from 100 kHz to 300 kHz.

In an embodiment, the one or more electric fields include an electric field strength selected from a range of electric field strengths from 0.25 V/cm to 1000 V/cm.

In an embodiment, the one or more electric fields include an electric field strength selected from a range of electric field strengths from 1 V/cm to 10 V/cm.

In an embodiment, the one or more electric fields include an electric field strength selected from a range of electric field strengths from 3 V/cm to 5 V/cm.

In an embodiment, a medical device for treating a cancerous tumor is included having a first lead can include a first wire, a second lead can include a second wire, a third lead can include a third wire, and a fourth lead can include a fourth wire; a first electrode in electrical communication with the first wire, a second electrode in electrical communication with the second wire, a third electrode in electrical communication with the third wire, and a fourth electrode in electrical communication with the fourth wire; wherein the first electrode and the third electrode form a supply electrode pair configured to deliver an electric field at or near a site of the cancerous tumor; and wherein the second electrode and the fourth electrode form a sensing electrode pair configured to measure impedance of the cancerous tumor independent of an impedance of the first electrode, the first wire, the third electrode, the third wire, and components in electrical communication therewith.

In an embodiment, the medical device can further include a fifth electrode in electrical communication with a fifth wire, a sixth electrode in electrical communication with a sixth wire, a seventh electrode in electrical communication with a seventh wire, and an eighth electrode in electrical communication with an eighth wire.

In an embodiment, a method for treating a cancerous tumor is included, the method including implanting a first lead and a second lead at or near a site of the cancerous tumor, the first lead can include a first wire and a second wire; and the second lead can include a third wire and a fourth wire; wherein the first wire is in electrical communication with a first electrode; the second wire is in electrical communication with a second electrode; the third wire is in electrical communication with a third electrode; and the fourth wire is in electrical communication with a fourth electrode; and wherein the first electrode and the third electrode form a first supply electrode pair configured to deliver an electric field at or near a site of the cancerous tumor, and the second electrode and fourth electrode form a first sensing electrode pair configured to measure impedance of the cancerous tumor independent of an impedance between the first sensing electrode pair applying a therapeutic electric field at or near a site of the cancerous tumor using the first supply electrode pair for a predetermined period of time; measuring the impedance of the cancerous tumor using the first sensing electrode pair.

In an embodiment, the cancerous tumor can include a cancerous cell population.

In an embodiment, a method can further include measuring an initial impedance of the cancerous tumor prior to beginning treating the cancerous tumor, wherein measuring the initial impedance includes applying a diagnostic electric field at or near the site of the cancerous tumor and recording the initial impedance.

In an embodiment, measuring the impedance of the cancerous tumor includes obtaining multiple measurements over a predetermined amount of time.

In an embodiment, a method can further include determining a regression of the cancerous tumor by detecting an increase in the impedance over the predetermined period of time.

In an embodiment, a method can further include determining a progression of the cancerous tumor by detecting a decrease in the impedance over the predetermined period of time.

In an embodiment, a method can further include adjusting the therapeutic electric field.

In an embodiment, measuring the impedance of the cancerous tumor includes obtaining multiple measurements over a predetermined amount of time.

In an embodiment, a method can further include determining a regression of the cancerous tumor by detecting an increase in the impedance over the predetermined period of time.

In an embodiment, a method can further include determining a progression of the cancerous tumor by detecting a decrease in the impedance over the predetermined period of time.

In an embodiment, a method can further include adjusting the therapeutic electric field.

In an embodiment, a medical device for treating a cancerous tumor is included having an electric field generating circuit configured to generate one or more electric fields; control circuitry in communication with the electric field generating circuit, the control circuitry configured to control delivery of the one or more electric fields from the electric field generating circuit; wherein the control circuitry causes the electric field generating circuit to generate one or more electric fields at frequencies selected from a range of between 10 kHz to 1 MHz at or near a site of the cancerous tumor; one or more supply leads in electrical communication with the electric field generating circuit, the one or more supply leads each can include one or more supply electrodes in electrical communication with the electric field generating circuit; and one or more sensing leads in electrical communication with the control circuitry, the one or more sensing leads each can include one or more sensing electrodes; and wherein the one or more sensing electrodes are configured to measure an impedance of the one or more supply electrodes.

In an embodiment, a medical device can further include a housing in which the electric field generating circuit and the control circuitry are disposed, wherein the housing includes a portion that is in electrical communication with the electric field generating circuit such that the housing serves as a supply electrode, wherein the one or more electric fields are delivered along at least one vector including a portion of the housing serving as a supply electrode.

In an embodiment, the one or more sensing electrodes are configured to perform unipolar impedance measurements to differentiate the impedance of each supply electrode.

In an embodiment, the one or more sensing electrodes are configured to perform unipolar impedance measurements to differentiate the impedance of each supply electrode.

In an embodiment, a method for treating a cancerous tumor is included, the method including implanting a first lead and a second lead at or near a site of the cancerous tumor; wherein the first lead and second lead each include one or more supply electrodes and one or more sensing electrodes; applying an electric field at or near the site of the cancerous tumor with the one or more supply electrodes for a predetermined period of time; measuring an impedance of each supply electrode using one or more sensing electrodes.

In an embodiment, a method can further include performing unipolar impedance measurements to differentiate the impedance of each supply electrode.

In an embodiment, a method for treating a cancerous tumor is included, the method implanting a first lead, a second lead, a third lead, and a fourth lead at or near a site of the cancerous tumor; wherein the first lead and third lead each include one or more supply electrodes, and the second lead and fourth lead each include one or more sensing electrodes; applying an electric field at or near the site of the cancerous tumor with the supply electrodes for a predetermined period of time; measuring an impedance of each supply electrode using the one or more sensing electrodes.

In an embodiment, a method can further include measuring a capacitance across the supply electrodes; wherein the measured capacitance can be used to determine a quality of the supply electrodes.

In an embodiment, a medical device for treating a cancerous tumor is included having an electric field generating circuit configured to generate one or more electric fields along a first vector; control circuitry in communication with the electric field generating circuit, the control circuitry configured to control delivery of the one or more electric fields from the electric field generating circuit; wherein the control circuitry causes the electric field generating circuit to generate one or more electric fields at frequencies selected from a range of between 10 kHz to 1 MHz at a site of the cancerous tumor; one or more supply leads in electrical communication with the electric field generating circuit, the one or more supply leads each can include one or more supply electrodes in electrical communication with the electric field generating circuit; and one or more sensing leads in electrical communication with the control circuitry, the one or more sensing leads each can include one or more sensing electrodes; and wherein the one or more sensing electrodes are configured to measure an impedance change in the one or more supply electrodes along a second vector that is different than the first vector along which the one or more electric fields are delivered to the cancerous tumor.

In an embodiment, a device can further include a housing in which the electric field generating circuit and the control circuitry are disposed, wherein the housing includes a portion that is in electrical communication with the electric field generating circuit to serve as a supply electrode, wherein the one or more electric fields are delivered along at least one vector including a portion of the housing serving as a supply electrode.

In an embodiment, the one or more sensing electrodes are configured to perform unipolar impedance measurements to differentiate the impedance of each supply electrode.

In an embodiment, measuring an impedance change in the one or more supply electrodes along a second vector includes measuring the impedance change along a second vector that is spatially separate from the first vector along which the one or more electric fields are delivered to the cancerous tumor by at least 30 degrees.

In an embodiment, measuring an impedance change in the one or more supply electrodes along a second vector includes measuring the impedance change along a second vector that is spatially separate from the first vector along which the one or more electric fields are delivered to the cancerous tumor by at least 60 degrees.

In an embodiment, measuring an impedance change in the one or more supply electrodes along a second vector includes measuring the impedance change along a second vector that is spatially separate from the first vector along which the one or more electric fields are delivered to the cancerous tumor by at least 90 degrees.

In an embodiment, each supply electrode and each sensing electrode is spatially separated along a longitudinal axis of the one or more leads by at least 0.25 cm.

In an embodiment, a medical device for treating a cancerous tumor is included having an electric field generating circuit configured to generate one or more electric fields along a first vector; control circuitry in communication with the electric field generating circuit, the control circuitry configured to control delivery of the one or more electric fields from the electric field generating circuit; wherein the control circuitry causes the electric field generating circuit to generate one or more electric fields at frequencies selected from a range of between 10 kHz to 1 MHz at a site of the cancerous tumor; one or more supply leads in electrical communication with the electric field generating circuit, the one or more supply leads each can include one or more supply electrodes in electrical communication with the electric field generating circuit; and one or more sensing leads in electrical communication with the control circuitry, the one or more sensing leads each can include one or more sensing electrodes; and wherein the one or more sensing electrodes are configured to measure an impedance change in the cancerous tumor along a second vector that is different than the first vector along which the one or more electric fields are delivered to the cancerous tumor.

In an embodiment, a method for treating a cancerous tumor is included, the method including implanting a first lead, a second lead, a third lead, and a fourth lead at or near a site of the cancerous tumor; wherein the first lead and third lead each include one or more supply electrodes, and the second lead and fourth lead each include one or more sensing electrodes; applying an electric field at or near the site of the cancerous tumor along a first vector with the one or more supply electrodes for a predetermined period of time; measuring the impedance of each supply electrode along a second vector using the one or more sensing electrodes; and wherein measuring the impedance of each supply electrode along a second vector includes measuring the impedance of each supply electrode along a second vector that is spatially separate from the first vector along which the one or more electric fields are delivered to the cancerous tumor.

In an embodiment, a method can further include performing unipolar impedance measurements to differentiate the impedance of each supply electrode.

In an embodiment, implanting any of the first lead, the second lead, the third lead, or the fourth lead at or near the site of the cancerous tumor includes delivery of any of the first lead, the second lead, the third lead, or the fourth lead through a natural body orifice or duct.

In an embodiment, the natural body orifice can be selected from any of a nasal passage, an ear canal, a mouth, an esophagus, a trachea, a urethra, a vagina, a small intestine, an anus, or a colon.

In an embodiment, the duct can be selected from any of a common bile duct, a bile duct, a pancreatic duct, a common hepatic duct, a ureter, a Eustachian tube, or a fallopian tube.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A medical device for treating a cancerous tumor comprising:
    a first lead comprising a first wire and a second wire;
    a second lead comprising a third wire and a fourth wire;
    a first electrode in electrical communication with the first wire, a second electrode in electrical communication with the second wire, a third electrode in electrical communication with the third wire, and a fourth electrode in electrical communication with the fourth wire;
    an electric field generating circuit configured to generate one or more electric fields at frequencies selected from a range of between 10 kHz to 1 MHz, wherein the one or more electric fields are effective to disrupt cellular mitosis in cancerous cells;
    a control circuitry in communication with the electric field generating circuit, wherein the control circuitry is configured to control delivery of the one or more electric fields from the electric field generating circuit;
    wherein the control circuitry causes the electric field generating circuit to generate the one or more electric fields at or near a site of the cancerous tumor located within a bodily tissue;
    wherein the first electrode and the third electrode form a supply electrode pair configured to deliver the one or more electric fields along a first vector at or near the site of the cancerous tumor;
    wherein the first lead and the second lead are each in electrical communication with the electric field generating circuit; and
    wherein the second electrode and the fourth electrode form a sensing electrode pair configured to measure an impedance of the cancerous tumor along a second vector independent of an impedance of the first electrode, the first wire, the third electrode, the third wire, and components in electrical communication therewith.

2. The medical device of claim 1, wherein the medical device is configured to be implanted entirely within a subject.

3. The medical device of claim 1, wherein the medical device is configured to be partially implanted within a subject.

4. The medical device of claim 1, wherein the one or more electric fields are delivered to the cancerous tumor at frequencies selected from a range of from 100 kHz to 300 kHz.

5. The medical device of claim 1, wherein a current flow through the second electrode, the second wire, the fourth electrode, the fourth wire, and components in electrical communication therewith is less than 100 pA.

6. The medical device of claim 1, wherein the first electrode and the second electrode of the first lead are spatially separated along a longitudinal axis of the first lead by at least 1 mm; and wherein the third electrode and the fourth electrode of the second lead are spatially separated along a longitudinal axis of the second lead by at least 1 mm.

7. The medical device of claim 1, wherein the one or more electric fields comprise an electric field strength selected from a range of electric field strengths from 0.25 V/cm to 1000 V/cm.

8. The medical device of claim 1, wherein the first electrode and the third electrode deliver the one or more electric fields along the first vector while the second electrode and the fourth electrode simultaneously measure the impedance of the cancerous tumor along the second vector.

* * * * *